United States Patent
Clauson et al.

(10) Patent No.: US 9,480,598 B2
(45) Date of Patent: Nov. 1, 2016

(54) EXPANDING OCULAR IMPLANT DEVICES AND METHODS

(71) Applicant: Transcend Medical, Inc., Menlo Park, CA (US)

(72) Inventors: Luke Clauson, Menlo Park, CA (US); Michael Schaller, Menlo Park, CA (US); David Lari, Menlo Park, CA (US)

(73) Assignee: Novartis AG, Basel (CH)

( * ) Notice: Subject to any disclaimer, the term of this patent is extended or adjusted under 35 U.S.C. 154(b) by 235 days.

(21) Appl. No.: 14/029,389

(22) Filed: Sep. 17, 2013

(65) Prior Publication Data

US 2014/0081195 A1    Mar. 20, 2014

Related U.S. Application Data

(60) Provisional application No. 61/702,179, filed on Sep. 17, 2012.

(51) Int. Cl.
*A61B 19/00* (2006.01)
*A61F 9/007* (2006.01)

(52) U.S. Cl.
CPC .... *A61F 9/00781* (2013.01); *A61F 2210/0014* (2013.01); *A61F 2250/001* (2013.01)

(58) Field of Classification Search
CPC .................................................. A61F 9/00781
USPC ..................... 604/8; 623/1.2, 1.29
See application file for complete search history.

(56) References Cited

U.S. PATENT DOCUMENTS

| | | | |
|---|---|---|---|
| 2,990,670 | A | 7/1961 | Kingsbury |
| 3,439,675 | A | 4/1969 | Cohen |
| 3,767,759 | A | 10/1973 | Wichterle |
| 3,788,327 | A | 1/1974 | Donowitz et al. |
| 3,915,172 | A | 10/1975 | Wichterle et al. |
| 4,037,604 | A | 7/1977 | Newkirk |
| 4,402,681 | A | 9/1983 | Haas et al. |
| 4,457,757 | A | 7/1984 | Molteno |
| 4,521,210 | A | 6/1985 | Wong |

(Continued)

FOREIGN PATENT DOCUMENTS

| | | |
|---|---|---|
| CN | 1225027 A | 8/1999 |
| CN | 1285724 A | 2/2001 |

(Continued)

OTHER PUBLICATIONS

Barsky et al. "Evaluation of absorbable gelatin film (Gelfilm) in cyclodialysis clefts" Arch. Ophth. 60(6): 1044-1052, 1958.

(Continued)

*Primary Examiner* — Leslie Deak
(74) *Attorney, Agent, or Firm* — Fred C. Hernandez; Mintz Levin Cohn Ferris Glovsky and Popeo, P.C.

(57) ABSTRACT

Disclosed herein are devices and methods related to implants for treating one or more physiological conditions of the eye. Some embodiments disclosed herein include an expandable ocular implant for implanting in an eye. The expandable implant can include an implant having an elongate tubular body and an expandable sheath securely adapted to a part of the implant. Some embodiments of the expandable sheath can have at least one expandable feature that can assist the expandable sheath in forming a compact and an expanded configuration.

20 Claims, 10 Drawing Sheets

(56) References Cited

U.S. PATENT DOCUMENTS

| | | |
|---|---|---|
| 4,554,918 A | 11/1985 | White |
| 4,604,087 A | 8/1986 | Joseph |
| 4,617,715 A | 10/1986 | Koistinen et al. |
| 4,634,418 A | 1/1987 | Binder |
| 4,722,724 A | 2/1988 | Schocket |
| 4,750,901 A | 6/1988 | Molteno |
| 4,787,885 A | 11/1988 | Binder |
| 4,826,478 A | 5/1989 | Schocket |
| 4,846,172 A | 7/1989 | Berlin |
| 4,863,457 A | 9/1989 | Lee |
| 4,886,488 A | 12/1989 | White |
| 4,900,300 A | 2/1990 | Lee |
| 4,930,512 A | 6/1990 | Henriksen et al. |
| 4,946,436 A | 8/1990 | Smith |
| 4,968,296 A | 11/1990 | Ritch et al. |
| 5,041,081 A | 8/1991 | Odrich |
| 5,071,408 A | 12/1991 | Ahmed |
| 5,073,163 A | 12/1991 | Lippman |
| 5,092,837 A | 3/1992 | Ritch et al. |
| 5,127,901 A | 7/1992 | Odrich |
| 5,171,213 A | 12/1992 | Price, Jr. |
| 5,178,604 A | 1/1993 | Baerveldt et al. |
| 5,180,362 A | 1/1993 | Worst |
| 5,284,476 A | 2/1994 | Koch |
| 5,300,020 A | 4/1994 | L'Esperance, Jr. |
| 5,338,291 A | 8/1994 | Speckman et al. |
| 5,342,370 A | 8/1994 | Simon et al. |
| 5,346,464 A | 9/1994 | Camras |
| 5,370,607 A | 12/1994 | Memmen |
| 5,372,577 A | 12/1994 | Ungerleider |
| 5,397,300 A | 3/1995 | Baerveldt et al. |
| 5,423,777 A | 6/1995 | Tajiri et al. |
| 5,433,701 A | 7/1995 | Rubinstein |
| 5,443,505 A | 8/1995 | Wong et al. |
| 5,454,746 A | 10/1995 | Guegan et al. |
| 5,476,445 A | 12/1995 | Baerveldt et al. |
| 5,558,629 A | 9/1996 | Baerveldt et al. |
| 5,558,630 A | 9/1996 | Fisher |
| RE35,390 E | 12/1996 | Smith |
| 5,601,094 A | 2/1997 | Reiss |
| 5,626,558 A | 5/1997 | Suson |
| 5,626,559 A | 5/1997 | Solomon |
| 5,651,782 A | 7/1997 | Simon et al. |
| 5,676,944 A | 10/1997 | Alvarado et al. |
| 5,702,414 A | 12/1997 | Richter et al. |
| 5,704,907 A | 1/1998 | Nordquist et al. |
| 5,713,844 A | 2/1998 | Peyman |
| 5,728,465 A | 3/1998 | Dorfman et al. |
| 5,741,292 A | 4/1998 | Mendius |
| 5,743,868 A | 4/1998 | Brown et al. |
| 5,749,879 A | 5/1998 | Middleman et al. |
| 5,752,928 A | 5/1998 | de Roulhac et al. |
| 5,792,075 A | 8/1998 | Schwager |
| 5,807,244 A | 9/1998 | Barot |
| 5,807,302 A | 9/1998 | Wandel |
| 5,868,697 A | 2/1999 | Richter et al. |
| 5,882,327 A | 3/1999 | Jacob |
| 5,893,837 A | 4/1999 | Eagles et al. |
| 5,941,250 A | 8/1999 | Aramant et al. |
| 5,968,058 A | 10/1999 | Richter et al. |
| 6,007,510 A | 12/1999 | Nigam |
| 6,007,511 A | 12/1999 | Prywes |
| 6,019,786 A | 2/2000 | Thompson |
| 6,036,678 A | 3/2000 | Giungo |
| 6,050,970 A | 4/2000 | Baerveldt |
| 6,050,999 A | 4/2000 | Paraschac et al. |
| 6,077,299 A | 6/2000 | Adelberg et al. |
| 6,102,045 A | 8/2000 | Nordquist et al. |
| 6,142,969 A | 11/2000 | Nigam |
| 6,152,918 A | 11/2000 | Padilla et al. |
| 6,174,307 B1 | 1/2001 | Daniel et al. |
| 6,186,974 B1 | 2/2001 | Allan et al. |
| 6,203,513 B1 | 3/2001 | Yaron et al. |
| 6,221,078 B1 | 4/2001 | Bylsma |
| 6,251,090 B1 | 6/2001 | Avery et al. |
| 6,261,256 B1 | 7/2001 | Ahmed |
| 6,264,668 B1 | 7/2001 | Prywes |
| 6,270,472 B1 | 8/2001 | Antaki et al. |
| 6,331,313 B1 | 12/2001 | Wong et al. |
| 6,375,642 B1 | 4/2002 | Grieshaber et al. |
| 6,383,219 B1 | 5/2002 | Telandro et al. |
| 6,450,984 B1 | 9/2002 | Lynch et al. |
| 6,464,724 B1 | 10/2002 | Lynch et al. |
| 6,468,283 B1 | 10/2002 | Richter et al. |
| 6,471,666 B1 | 10/2002 | Odrich |
| 6,471,777 B1 | 10/2002 | Kobayashi et al. |
| 6,494,857 B1 | 12/2002 | Neuhann |
| 6,508,779 B1 | 1/2003 | Suson |
| 6,510,600 B2 | 1/2003 | Yaron et al. |
| 6,524,275 B1 | 2/2003 | Lynch et al. |
| 6,533,768 B1 | 3/2003 | Hill |
| 6,537,568 B2 | 3/2003 | Olejnik et al. |
| 6,544,208 B2 | 4/2003 | Ethier et al. |
| 6,544,249 B1 | 4/2003 | Yu et al. |
| 6,558,342 B1 | 5/2003 | Yaron et al. |
| 6,561,974 B1 | 5/2003 | Grieshaber et al. |
| 6,579,256 B2 | 6/2003 | Hughes |
| 6,589,203 B1 | 7/2003 | Mitrev |
| 6,595,945 B2 | 7/2003 | Brown |
| 6,626,858 B2 | 9/2003 | Lynch et al. |
| 6,638,239 B1 | 10/2003 | Bergheim et al. |
| 6,648,283 B2 | 11/2003 | Chase et al. |
| 6,666,841 B2 | 12/2003 | Gharib et al. |
| 6,676,607 B2 | 1/2004 | de Juan, Jr. et al. |
| 6,699,210 B2 | 3/2004 | Williams et al. |
| 6,699,211 B2 | 3/2004 | Savage |
| 6,719,750 B2 | 4/2004 | Varner et al. |
| 6,726,664 B2 | 4/2004 | Yaron et al. |
| 6,726,676 B2 | 4/2004 | Stegmann et al. |
| 6,730,056 B1 | 5/2004 | Ghaem et al. |
| 6,736,791 B1 | 5/2004 | Tu et al. |
| 6,741,666 B1 | 5/2004 | Henry et al. |
| 6,752,753 B1 | 6/2004 | Hoskins et al. |
| 6,780,164 B2 | 8/2004 | Bergheim et al. |
| 6,783,544 B2 | 8/2004 | Lynch et al. |
| 6,786,888 B1 | 9/2004 | Zadno-Azizi et al. |
| 6,827,699 B2 | 12/2004 | Lynch et al. |
| 6,827,700 B2 | 12/2004 | Lynch et al. |
| 6,881,197 B1 | 4/2005 | Nigam |
| 6,881,198 B2 | 4/2005 | Brown |
| 6,939,298 B2 | 9/2005 | Brown et al. |
| 6,955,656 B2 | 10/2005 | Bergheim et al. |
| 6,962,573 B1 | 11/2005 | Wilcox |
| 6,966,888 B2 | 11/2005 | Cullen et al. |
| 6,969,384 B2 | 11/2005 | de Juan, Jr. et al. |
| 6,981,958 B1 | 1/2006 | Gharib et al. |
| 6,989,007 B2 | 1/2006 | Shadduck |
| 7,041,077 B2 | 5/2006 | Shields |
| 7,090,681 B2 | 8/2006 | Weber et al. |
| 7,094,225 B2 | 8/2006 | Tu et al. |
| 7,135,009 B2 | 11/2006 | Tu et al. |
| 7,160,264 B2 | 1/2007 | Lisk, Jr. et al. |
| 7,163,543 B2 | 1/2007 | Smedley et al. |
| 7,186,232 B1 | 3/2007 | Smedley et al. |
| 7,192,412 B1 | 3/2007 | Zhou et al. |
| 7,195,774 B2 | 3/2007 | Carvalho et al. |
| 7,207,965 B2 | 4/2007 | Simon |
| 7,220,238 B2 | 5/2007 | Lynch et al. |
| 7,273,475 B2 | 9/2007 | Tu et al. |
| 7,291,125 B2 | 11/2007 | Coroneo |
| 7,297,130 B2 | 11/2007 | Bergheim et al. |
| 7,331,984 B2 | 2/2008 | Tu et al. |
| 7,431,710 B2 | 10/2008 | Tu et al. |
| 7,488,303 B1 | 2/2009 | Haffner et al. |
| 7,563,241 B2 | 7/2009 | Tu et al. |
| 7,708,711 B2 | 5/2010 | Tu et al. |
| 7,850,637 B2 | 12/2010 | Lynch et al. |
| 7,857,782 B2 | 12/2010 | Tu et al. |
| 7,867,186 B2 | 1/2011 | Haffner et al. |
| 7,867,205 B2 | 1/2011 | Bergheim et al. |
| 7,972,616 B2 * | 7/2011 | Dubrow et al. ............ 424/423 |
| 8,075,511 B2 | 12/2011 | Tu et al. |
| 8,128,588 B2 | 3/2012 | Coroneo |
| 8,337,393 B2 | 12/2012 | Silverstrini et al. |

(56) References Cited

U.S. PATENT DOCUMENTS

| | | |
|---|---|---|
| 8,702,727 B1 | 4/2014 | Harrington et al. |
| 8,721,656 B2 | 5/2014 | De Juan, Jr. et al. |
| 2001/0000527 A1 | 4/2001 | Yaron et al. |
| 2001/0025150 A1 | 9/2001 | de Juan et al. |
| 2002/0013546 A1 | 1/2002 | Grieshaber et al. |
| 2002/0013572 A1 | 1/2002 | Berlin |
| 2002/0026200 A1 | 2/2002 | Savage |
| 2002/0072673 A1 | 6/2002 | Yamamoto et al. |
| 2002/0087111 A1 | 7/2002 | Ethier et al. |
| 2002/0111608 A1 | 8/2002 | Baerveldt et al. |
| 2002/0128613 A1 | 9/2002 | Nakayama |
| 2002/0133168 A1 | 9/2002 | Smedley et al. |
| 2002/0143284 A1 | 10/2002 | Tu et al. |
| 2002/0156413 A1 | 10/2002 | Williams et al. |
| 2002/0165478 A1 | 11/2002 | Gharib et al. |
| 2002/0169130 A1 | 11/2002 | Tu et al. |
| 2002/0169468 A1 | 11/2002 | Brown |
| 2002/0177856 A1 | 11/2002 | Richter et al. |
| 2002/0188308 A1 | 12/2002 | Tu et al. |
| 2002/0193725 A1 | 12/2002 | Odrich |
| 2002/0193804 A1 | 12/2002 | Tickle |
| 2003/0009124 A1 | 1/2003 | Lynch et al. |
| 2003/0028127 A1 | 2/2003 | Balzum et al. |
| 2003/0028228 A1 | 2/2003 | Sand |
| 2003/0055372 A1 | 3/2003 | Lynch et al. |
| 2003/0060752 A1 | 3/2003 | Bergheim et al. |
| 2003/0069637 A1 | 4/2003 | Lynch et al. |
| 2003/0088260 A1 | 5/2003 | Smedley et al. |
| 2003/0097151 A1 | 5/2003 | Smedley et al. |
| 2003/0097171 A1 | 5/2003 | Elliott |
| 2003/0120200 A1 | 6/2003 | Bergheim et al. |
| 2003/0135149 A1 | 7/2003 | Cullen et al. |
| 2003/0181848 A1 | 9/2003 | Bergheim et al. |
| 2003/0187384 A1 | 10/2003 | Bergheim et al. |
| 2003/0187385 A1 | 10/2003 | Bergheim et al. |
| 2003/0191428 A1 | 10/2003 | Bergheim et al. |
| 2003/0208163 A1 | 11/2003 | Yaron et al. |
| 2003/0220602 A1 | 11/2003 | Lynch et al. |
| 2003/0220603 A1 | 11/2003 | Lynch et al. |
| 2003/0229303 A1 | 12/2003 | Haffner et al. |
| 2003/0232015 A1 | 12/2003 | Brown et al. |
| 2003/0236483 A1 | 12/2003 | Ren |
| 2003/0236484 A1 | 12/2003 | Lynch et al. |
| 2004/0015140 A1 | 1/2004 | Shields |
| 2004/0024345 A1 | 2/2004 | Gharib et al. |
| 2004/0050392 A1 | 3/2004 | Tu et al. |
| 2004/0073156 A1 | 4/2004 | Brown |
| 2004/0088048 A1 | 5/2004 | Richter et al. |
| 2004/0092856 A1 | 5/2004 | Dahan |
| 2004/0097984 A1 | 5/2004 | Zapata |
| 2004/0102729 A1 | 5/2004 | Haffner et al. |
| 2004/0106977 A1 | 6/2004 | Sullivan et al. |
| 2004/0111050 A1 | 6/2004 | Smedley et al. |
| 2004/0127843 A1 | 7/2004 | Tu et al. |
| 2004/0147870 A1 | 7/2004 | Burns et al. |
| 2004/0148022 A1 | 7/2004 | Eggleston |
| 2004/0193095 A1 | 9/2004 | Shadduck |
| 2004/0193262 A1 | 9/2004 | Shadduck |
| 2004/0210181 A1 | 10/2004 | Vass et al. |
| 2004/0210185 A1 | 10/2004 | Tu et al. |
| 2004/0216749 A1 | 11/2004 | Tu |
| 2004/0225250 A1 | 11/2004 | Yablonski |
| 2004/0236343 A1 | 11/2004 | Taylor et al. |
| 2004/0249333 A1 | 12/2004 | Bergheim et al. |
| 2004/0254517 A1 | 12/2004 | Quiroz-Mercado et al. |
| 2004/0254519 A1 | 12/2004 | Tu et al. |
| 2004/0254520 A1 | 12/2004 | Porteous et al. |
| 2004/0254521 A1 | 12/2004 | Simon |
| 2004/0260227 A1 | 12/2004 | Lisk et al. |
| 2004/0260228 A1 | 12/2004 | Lynch et al. |
| 2005/0008673 A1 | 1/2005 | Snyder et al. |
| 2005/0038334 A1 | 2/2005 | Lynch et al. |
| 2005/0049578 A1 | 3/2005 | Tu et al. |
| 2005/0085892 A1 | 4/2005 | Goto et al. |
| 2005/0090806 A1 | 4/2005 | Lynch et al. |
| 2005/0090807 A1 | 4/2005 | Lynch et al. |
| 2005/0101967 A1 | 5/2005 | Weber et al. |
| 2005/0107734 A1 | 5/2005 | Coroneo |
| 2005/0119601 A9 | 6/2005 | Lynch et al. |
| 2005/0119636 A1 | 6/2005 | Haffner et al. |
| 2005/0119737 A1 | 6/2005 | Bene et al. |
| 2005/0125003 A1 | 6/2005 | Pinchuk et al. |
| 2005/0143817 A1 | 6/2005 | Hunter et al. |
| 2005/0149080 A1 | 7/2005 | Hunter et al. |
| 2005/0171507 A1 | 8/2005 | Christian et al. |
| 2005/0175663 A1 | 8/2005 | Hunter et al. |
| 2005/0181011 A1 | 8/2005 | Hunter et al. |
| 2005/0181977 A1 | 8/2005 | Hunter et al. |
| 2005/0182350 A1 | 8/2005 | Nigam |
| 2005/0191331 A1 | 9/2005 | Hunter et al. |
| 2005/0192527 A1 | 9/2005 | Gharib et al. |
| 2005/0197613 A1 | 9/2005 | Sniegowski et al. |
| 2005/0209549 A1 | 9/2005 | Bergheim et al. |
| 2005/0209550 A1 | 9/2005 | Bergheim et al. |
| 2005/0232972 A1 | 10/2005 | Odrich |
| 2005/0244462 A1 | 11/2005 | Farooq |
| 2005/0245911 A1 | 11/2005 | Wright et al. |
| 2005/0250788 A1 | 11/2005 | Tu et al. |
| 2005/0266047 A1 | 12/2005 | Tu et al. |
| 2005/0267397 A1 | 12/2005 | Bhalla |
| 2005/0267398 A1 | 12/2005 | Protopsaltis et al. |
| 2005/0271704 A1 | 12/2005 | Tu et al. |
| 2005/0273033 A1 | 12/2005 | Grahn et al. |
| 2005/0277864 A1 | 12/2005 | Haffner et al. |
| 2005/0283108 A1 | 12/2005 | Savage |
| 2005/0288617 A1 | 12/2005 | Yaron et al. |
| 2005/0288619 A1 | 12/2005 | Gharib et al. |
| 2006/0004348 A1 | 1/2006 | Scheller et al. |
| 2006/0020248 A1 | 1/2006 | Prescott |
| 2006/0032507 A1 | 2/2006 | Tu |
| 2006/0036207 A1 | 2/2006 | Koonmen et al. |
| 2006/0047263 A1 | 3/2006 | Tu et al. |
| 2006/0069340 A1 | 3/2006 | Simon |
| 2006/0074375 A1 | 4/2006 | Bergheim et al. |
| 2006/0084907 A1 | 4/2006 | Bergheim et al. |
| 2006/0116626 A1 | 6/2006 | Smedley et al. |
| 2006/0149194 A1 | 7/2006 | Conston et al. |
| 2006/0155238 A1 | 7/2006 | Shields |
| 2006/0173397 A1 | 8/2006 | Tu et al. |
| 2006/0195055 A1 | 8/2006 | Bergheim et al. |
| 2006/0195056 A1 | 8/2006 | Bergheim et al. |
| 2006/0200113 A1 | 9/2006 | Haffner et al. |
| 2006/0235367 A1 | 10/2006 | Takashima et al. |
| 2006/0241580 A1 | 10/2006 | Mittelstein et al. |
| 2006/0241749 A1 | 10/2006 | Tu et al. |
| 2006/0276739 A1 | 12/2006 | Brown |
| 2007/0010827 A1 | 1/2007 | Tu et al. |
| 2007/0088242 A1 | 4/2007 | Coroneo |
| 2007/0088424 A1 | 4/2007 | Greenberg et al. |
| 2007/0088432 A1 | 4/2007 | Solovay et al. |
| 2007/0106235 A1 | 5/2007 | Coroneo |
| 2007/0106236 A1 | 5/2007 | Coroneo |
| 2007/0112292 A1 | 5/2007 | Tu et al. |
| 2007/0118147 A1 | 5/2007 | Smedley et al. |
| 2007/0129717 A1* | 6/2007 | Brown, III ............ A61B 5/015 606/41 |
| 2007/0149915 A1 | 6/2007 | Yablonski |
| 2007/0191863 A1 | 8/2007 | De Juan et al. |
| 2007/0276315 A1 | 11/2007 | Haffner et al. |
| 2007/0276316 A1 | 11/2007 | Haffner et al. |
| 2007/0282244 A1 | 12/2007 | Tu et al. |
| 2007/0282245 A1 | 12/2007 | Tu et al. |
| 2007/0293807 A1 | 12/2007 | Lynch et al. |
| 2008/0015488 A1 | 1/2008 | Tu et al. |
| 2008/0045878 A1 | 2/2008 | Bergheim et al. |
| 2008/0058704 A1 | 3/2008 | Hee et al. |
| 2008/0108933 A1 | 5/2008 | Yu et al. |
| 2008/0147021 A1 | 6/2008 | Jani |
| 2008/0151188 A1 | 6/2008 | Kawai et al. |
| 2008/0195027 A1 | 8/2008 | Coroneo |
| 2008/0200860 A1 | 8/2008 | Tu et al. |
| 2008/0228127 A1 | 9/2008 | Burns et al. |
| 2008/0234624 A2 | 9/2008 | Bergheim et al. |
| 2009/0036819 A1 | 2/2009 | Tu et al. |

(56) References Cited

U.S. PATENT DOCUMENTS

| | | |
|---|---|---|
| 2009/0036840 A1 | 2/2009 | Viray et al. |
| 2009/0043321 A1 | 2/2009 | Conston et al. |
| 2009/0138022 A1 | 5/2009 | Tu et al. |
| 2009/0171358 A1 | 7/2009 | Chang et al. |
| 2009/0182421 A1 | 7/2009 | Silvestrini et al. |
| 2010/0010416 A1 | 1/2010 | Juan, Jr. et al. |
| 2010/0134759 A1 | 6/2010 | Silvestrini et al. |
| 2010/0137981 A1* | 6/2010 | Silvestrini et al. ............ 623/4.1 |
| 2010/0152641 A1 | 6/2010 | Yablonski |
| 2010/0211079 A1 | 8/2010 | Aramant |
| 2010/0234790 A1 | 9/2010 | Tu et al. |
| 2010/0274259 A1 | 10/2010 | Yaron et al. |
| 2010/0280317 A1 | 11/2010 | Silvestrini et al. |
| 2011/0028883 A1* | 2/2011 | Juan et al. .................. 604/8 |
| 2011/0028884 A1 | 2/2011 | Coroneo |
| 2011/0087149 A1 | 4/2011 | Coroneo |
| 2011/0087150 A1 | 4/2011 | Coroneo |
| 2011/0087151 A1 | 4/2011 | Coroneo |
| 2011/0098629 A1 | 4/2011 | Juan, Jr. et al. |
| 2011/0098809 A1 | 4/2011 | Wardle et al. |
| 2011/0276054 A1 | 11/2011 | Helmy |
| 2011/0288525 A1 | 11/2011 | Hallen et al. |
| 2011/0306915 A1 | 12/2011 | De Juan, Jr. et al. |
| 2011/0319806 A1 | 12/2011 | Wardle |
| 2012/0035524 A1* | 2/2012 | Silvestrini .................. 604/8 |
| 2012/0035525 A1 | 2/2012 | Silvestrini |
| 2012/0089071 A1 | 4/2012 | Oliver et al. |
| 2012/0116504 A1 | 5/2012 | Lyons et al. |
| 2012/0123316 A1 | 5/2012 | Horvath et al. |
| 2012/0123434 A1 | 5/2012 | Grabner et al. |
| 2012/0271272 A1 | 10/2012 | Hammack et al. |
| 2014/0155805 A1 | 6/2014 | Schaller et al. |

FOREIGN PATENT DOCUMENTS

| | | |
|---|---|---|
| CN | 1124164 C | 10/2003 |
| CN | 1681457 A | 10/2005 |
| EP | 0 228 185 A1 | 11/1986 |
| EP | 1184010 A2 | 3/2002 |
| EP | 1310222 A2 | 5/2003 |
| EP | 1473004 A2 | 11/2004 |
| EP | 1477146 A2 | 11/2004 |
| EP | 1418868 B1 | 3/2008 |
| EP | 1977724 A1 | 10/2008 |
| EP | 2027837 A2 | 2/2009 |
| GB | 2101891 A | 1/1983 |
| JP | 2007-535386 A | 12/2007 |
| JP | 2010-533565 A | 10/2010 |
| RU | 2018289 C1 | 8/1994 |
| RU | 2056818 C1 | 3/1996 |
| RU | 2074686 C1 | 3/1997 |
| RU | 2074687 C1 | 3/1997 |
| RU | 2157678 C1 | 10/2000 |
| WO | WO-89/00869 A1 | 2/1989 |
| WO | WO-91/12046 A1 | 8/1991 |
| WO | WO-92/19294 A1 | 11/1992 |
| WO | WO-94/02081 A1 | 2/1994 |
| WO | WO-94/09721 A1 | 5/1994 |
| WO | WO-94/09837 A1 | 5/1994 |
| WO | WO-94/13234 A1 | 6/1994 |
| WO | WO-95/08310 A1 | 3/1995 |
| WO | WO-95/13765 A1 | 5/1995 |
| WO | WO-96/20742 A1 | 7/1996 |
| WO | WO-96/36377 A1 | 11/1996 |
| WO | WO-98/23237 A1 | 6/1998 |
| WO | WO-98/30181 A1 | 7/1998 |
| WO | WO-99/26567 A1 | 6/1999 |
| WO | WO-00/06223 A1 | 2/2000 |
| WO | WO-00/64389 A1 | 11/2000 |
| WO | WO-00/64390 A1 | 11/2000 |
| WO | WO-00/64391 A1 | 11/2000 |
| WO | WO-00/64393 A1 | 11/2000 |
| WO | WO-00/64511 A1 | 11/2000 |
| WO | WO-01/78631 A2 | 10/2001 |
| WO | WO-01/78656 A2 | 10/2001 |
| WO | WO-01/97727 A1 | 12/2001 |
| WO | WO-02/36052 | 5/2002 |
| WO | WO-02/070045 A1 | 9/2002 |
| WO | WO-02/074052 A2 | 9/2002 |
| WO | WO-02/080811 A2 | 10/2002 |
| WO | WO-02/080829 A2 | 10/2002 |
| WO | WO-02/087418 A2 | 11/2002 |
| WO | WO-02/087479 A2 | 11/2002 |
| WO | WO-02/089699 A2 | 11/2002 |
| WO | WO-02/102274 A2 | 12/2002 |
| WO | WO-03/015659 A2 | 2/2003 |
| WO | WO-03/015667 A1 | 2/2003 |
| WO | WO-03/041622 A2 | 5/2003 |
| WO | WO-03/073968 A2 | 9/2003 |
| WO | WO-03/099175 A1 | 12/2003 |
| WO | WO-2004/014218 A2 | 2/2004 |
| WO | WO-2004/026106 A2 | 4/2004 |
| WO | WO-2004/026347 A2 | 4/2004 |
| WO | WO-2004/043231 A2 | 5/2004 |
| WO | WO-2004/056294 A1 | 7/2004 |
| WO | WO-2004/060219 A1 | 7/2004 |
| WO | WO-2004/062469 A2 | 7/2004 |
| WO | WO-2004/073552 A2 | 9/2004 |
| WO | WO-2004/110391 A2 | 12/2004 |
| WO | WO-2005/016418 A1 | 2/2005 |
| WO | WO-2005/046782 A1 | 5/2005 |
| WO | WO-2005/055873 A2 | 6/2005 |
| WO | WO-2005/105197 A2 | 11/2005 |
| WO | WO-2005/107664 A2 | 11/2005 |
| WO | WO-2005/107845 A1 | 11/2005 |
| WO | WO-2006/012421 A2 | 2/2006 |
| WO | WO-2006/036715 A2 | 4/2006 |
| WO | WO-2007/087061 A2 | 8/2007 |
| WO | WO-2007/115259 A2 | 10/2007 |
| WO | WO-2007/130393 A2 | 11/2007 |
| WO | WO-2008/061043 | 5/2008 |
| WO | WO-2009/012406 A1 | 1/2009 |
| WO | WO-2009/035562 A2 | 3/2009 |
| WO | WO-2009/158524 A2 | 12/2009 |
| WO | WO-2010/065970 A1 | 6/2010 |
| WO | WO-2010/115101 A1 | 10/2010 |
| WO | WO-2012/019136 A2 | 2/2012 |

OTHER PUBLICATIONS

Bick MW "Use of tantalum for ocular drainage" Arch Ophthal. 42(4): 373-88 (1949).

Bietti "The present state of the use of plastics in eye surgery" Acta Ophthalmol (Copenh) 33(4):337-70 (1955).

Brown et al., "Internal Sclerectomy for Glaucoma Filtering Surgery with an Automated Trephine," Archives of Ophthalmology, 105:133-136 (1987).

Burchfield JC, Kass MA, Wax MB. Primary valve malfunction of the Krupin eye valve with disk. J Glaucoma. Jun. 1997;6(3):152-6.

Chiou et al. "Ultrasound biomicroscopy of eyes undergoing deep sclerectomy with collagen implant" Br J Ophthalmol 80 (1996), pp. 541-544.

Chylack LT, Bellows AR. Molecular sieving in suprachoroidal fluid formation in man. Invest Ophthalmol Vis Sci 17: 420, 1978.

Classen et al. "A histopathologic and immunohistorchemical analysis of the filtration bleb after unsuccessful glaucoma seton implantation" Am. J. Ophthalmol. 122:205-12 (1996).

Cohen et al. "First day post-operative review following uncomplicated phacoemulsification" Eye 12(4):634-6 (1998).

Collaborative Normal-Tension Study Group. Comparison of glaucomatous progression between untreated patients with normal-tension glaucoma and patients with therapeutically reduced intraocular pressures. Am J Ophthalmol 1998;126:487-97.

Congdon N, O'Colmain B, Klaver CC, et al. Causes and prevalence of visual impairment among adults in the United States. Arch Ophthalmol 2004;122:477-85.

Coote. "Glaucoma Hollow Fiber Filters—A New Glaucoma Seton. Preliminary Results." J. Glaucoma. vol. 8 No. 1 Supplement (1999):p. S4.

(56) References Cited

OTHER PUBLICATIONS

Cullen, et al. "Anterior Chamber of Frontal Sinus Shunt for the Diversion of Aqueous Humor: A Pilot Study in Four Normal Dogs". *Veterinary Ophthalmology*. vol. 1. No. 1. (1998):31-39.

Demailly et al. "Non-penetrating deep sclerectomy (NPDS) with or without collagen device (CD) in primary open-angle glaucoma: middle-term retrospective study" International Ophthalmology 20: 131-140, 1997.

Derwent English abstract for EP 1184010, published Mar. 6, 2002 entitled: "Drainage unit for an eye, consists of a hollow line, a distribution member, and a pressure relief valve which only allows water to leave the eye chamber above a certain pressure," Accession Nbr. 12409716 [351].

Dinakaran et al. "Is the first post-operative day review necessary following uncomplicated phacoemulsification surgery?" Eye, 14(3A):364-6 (2000).

Draeger "Chirurgische Maßnahmen bei kongenitalem Glaukom" (Surgical Interventions in Congenital Glaucoma) Klin Monatsbl Augenheilkd 1993; 202(5): 425-427 [Article in German with English summary included].

Einmahl et al. "Evaluation of a novel biomaterial in the suprachoroidal space of the rabbit eye" Invest Ophthalmol Vis Sci. 43:1533-1539 (2002).

Ellis, RA "A Reduction of Intraocular Pressure Using Plastics in Surgery" Am J Ophth. 50; 1960, 733-742.

Emi et al. "Hydrostatic pressure of the suprachoroidal space" Invest. Ophthal. Visual Sci. 30(2):233-238 (1989).

Fanous MM, Cohn RA. Propionibacterium endophthalmitis following Molteno tube repositioning. J Glaucoma. Aug. 1997;6(4):201-2.

Friedman DS, Wolfs RC, O'Colmain BJ, et al. Prevalence of open-angle glaucoma among adults in the United States. Arch Ophthalmol 2004;122:532-8.

Fuchs E. "Detachment of the choroid inadvertently during cataract surgery" [German] von Graefes Arch Ophthalmol, 51:199-224 (1900) [Article in German with English summary].

G. Van Der Veen et al. "The Gonioseton, a surgical treatment for chronic glaucoma" Documenta Ophthalmologica Oct. 1990, vol. 75, Issue 3-4, pp. 365-375.

Gills et al. "Action of cyclodialysis utilizing an implant studied by manometry in a human eye" Exp Eye Res 1967; 6:75-78.

Gills JP "Cyclodialysis implants" South Med J. 1967 60(7):692-5.

Gills, "Cyclodialysis Implants in Human Eyes" Am J Ophth 61:1966,841-846.

Goldberg "Management of Uncontrolled Glaucoma With the Molteno System" Australian and New Zealand Journal of Ophthalmology 1987; 15: 97-107.

Gordon MO, Kass. MA, for the Ocular Hypertension Treatment Study Group. The Ocular Hypertension Treatment Study. Design and baseline description of the participants. Arch Ophthalmol 1999:573-83.

Grant, W.M., MD, Further Studies on Facility of Flow Through the Trabecular Meshwork, A.M.A. Archives of Ophthalmololgy, Oct. 1958, vol. 60, pp. 523-533.

Gross et al. "Surgical therapy of chronic glaucoma in aphakia and pseudophakia" Ophthalmology, 95:1195-201 (1988).

Harper SL, Foster CS. Intraocular lens explantation in uveitis. Int Ophthalmol Clin. 2000 Winter; 40(1):107-16.

Harrington "Cataract and Glaucoma. Management of the coexistent conditions and a description of a new operation combining lens extraction with reverse cyclodialysis." Am J Ophthalmol. May 1966;61(5 Pt 2):1134-40.

Heijl A, Leske MC, Bengtsson B, et al for the Early Manifest Glaucoma Trial Group. Reduction of intraocular pressure and glaucoma progression. Results from the Early Manifest Glaucoma Trial. Arch Ophthalmol 2002;120:1268-79.

Heine I. "Cyclodialysis, a new glaucoma operation" [German] Dtsch Med Wochenschr, 31:824-826 (1905).

Hildebrand et al. "Efficacy of anterior chamber decompression in controlling early intraocular pressure spikes after uneventful phacoemulsification" J. Catact Refract Surg., 29:1087-92 (2003).

Hoskins, et al., "Aqueous Humor Outflow", Becker-Shaffer's Diagnosis and Therapy of the Glaucomas, 6th Edition, Chapter 4, pp. 41-66, 1989.

Howorth D J "Feasibility study for a micromachined glaucoma drainage device" Cranfield University School of industrial and manufacturing science MSc Thesis Academic Year 2001-2002 Sep. 13, 2002.

Hylton et al. "Update on prostaglandin analogs" Curr Opin Ophthalmol, 14:65-9 (2003).

Javitt JC, Chiang YP. Preparing for managed competition. Utilization of ambulatory eye care visits to ophthalmologists. Arch Ophthalmol 1993;111:1034-5.

Jay JL, Allan D. The benefit of early trabeculectomy versus conventional management in primary open-angle glaucoma relative to severity of disease. Eye 1989; 3:528-35.

Jordan J. "A Novel Approach to Suprachoroidal Drainage for the Surgical Treatment of Intractable Glaucoma" J. Glaucoma 15:200-205 (2006).

Jordan JF, Dietlein TS, Dinslage S, Luke C, Konen W, Krieglstein GK. Cyclodialysis ab inferno as a surgical approach to intractable glaucoma. Graefes Arch Clin Exp Ophthalmol. Aug. 2007;245(8):1071-6.

Karlen et al. "Deep sclerectomy with collagen implant: medium term results" Br. J. Ophthalmol, Jan. 1999, 83(1):6-11.

Kass MA, Heuer DK, Higginbotham EJ, et al for the Ocular Hypertension Treatment Study Group. The Ocular HypertensionTreatment Study. A randomized trial determines that topical ocular hypotensive medication delays or prevents the onset of primary open-angle glaucoma. Arch Ophthalmol 2002;120:701-13.

Klemm et al. "Die Ultraschallbiomikroskopie als Kriterium der Funktionsprüfung des suprachorioidalen Spaltes nach kammerwinkelchirurgischen Eingriffen ; (Ultrasound Biomicroscopic Imaging for Assessment of the Suprachoroidal Cleft after Angle Surgery)" Klinische Monatsblätter für Augenheilkunde 1997; 210: 74-77 [Article in German with English summary included].

Klemm et al. "Experimental use of space-retaining substances with extended duration: functional and morphological results" Graefes Arch Clin Exp Ophthalmol Sep. 1995; 233(9):592-7.

Kozlov et al. "Nonpenetrating deep sclerectomy with collagen" Eye microsurgery 3:44-46 (1990) [Russian with English translation].

Krejci "Cyclodialysis with hydroxymethyl methacrylate capillary strip (HCS). Animal experiments with a new approach in glaucoma drainage surgery" Ophthalmologica 1972; 164(2):113-21.

Krejcí L. "Microdrainage of anterior chamber of eye glaucoma operation using hydron capillary drain." Acta Univ Carol Med Monogr. 1974;(61):1-90.

Kupfer "Studies on intraocular pressure. I. A technique for polyethylene tube implantation into the anterior chamber of the rabbit." Arch Ophthalmol. Apr. 1961;65:565-70.

La Rocca "Gonioplasty in Glaucoma*A Preliminary Report" Br J Ophth 46:1962, 404-415.

Law et al., "Retinal Complications After Aqueous Shunt Surgical Procedures for Glaucoma" Arch Ophthal.; Dec. 1996; vol. 114:1473-1480.

Lee et al. "Aqueous-venous shunt and intraocular pressure. Preliminary report of animal studies." *Investigative Ophthalmology*. vol. 5 No. 1: 59-64. Feb. 1966.

Lee et al. "Magnetic resonance imaging of the aqueous flow in eyes implanted with the trabeculo-suprachoroidal glaucoma seton" Invest. Ophthalmol. Vis. Sci. 33:948 (1992).

Lee KY. Trabeculo-suprachoroidal shunt for treating recalcitrant and secondary glaucoma. Presented at the American Academy of Ophthalmology Annual Meeting, Anaheim, CA, 1991.

Leske MC, Heijl A, Hussein M, et al for the Early Manifest Glaucoma Trial Group. Factors for glaucoma progression and the effect of treatment. The Early Manifest Glaucoma Trial. Arch Ophthalmol Jan. 2003;121:48-56.

Lichter PR, Musch DC, Gillespie BW, et al and the CIGTS Study Group. Interim clinical outcomes in the Collaborative Initial Glaucoma Treatment Study comparing initial treatment randomized to medications or surgery. Ophthalmology 2001;108:1943-53.

(56) References Cited

OTHER PUBLICATIONS

Losche W. "Proposals for improvement of cyclodialysis" Klin Monatsblatter Augenheilkd Augenarztl Fortbild 121(6):715-6 (1952) [German].

Marx et al., "Use of the Ganciclovir Implant in the Treatment of Recurrent Cytomegalovirus Retinitis" Arch Ophthal.; Jul. 1996; vol. 114:815-820.

McPherson "Combined Trabeculotomy and Cataract Extraction as a Single Operation*" Tr. Am. Ophth. Soc., vol. LXXIV, 1976; 251-260.

Migdal C, Gregory W, Hitchings R. Long term functional outcome after early surgery compared with laser and medicine in open-angle glaucoma. Ophthalmology 1994;101:1651-7.

Miglior S, Pfeiffer N, Zeyen T et al for the European Glaucoma Prevention Study Group. Results of the European Glaucoma Prevention Study. Ophthalmology 2005;112:366-75.

Miglior S, Zeyen T, Pfeiffer N, et al for the European Glaucoma Prevention Study Group. The European Glaucoma Prevention Study design and baseline description of the participants. Ophthalmology 2002;109:1612-21.

Miki, MD et al., "Intraocular Cannula for Continuous, Chronic Drug Delivery-Histopathic Observations and Function" Arch Ophthal.; May 1985; vol. 103:712-717.

Molteno et al. "Long tube implants in the management of glaucoma" South African Medical Journal, Jun. 26, 1976;50(27):1062-6.

Molteno et al. "The Vicryl tie technique for inserting a draining implant in the treatment of secondary glaucoma." Australian and New Zealand Journal of Ophthalmology 1986; 14: 343-354.

Moses RA "Detachment of ciliary body-anatomical and physical considerations" Investigative Ophthalmology & Visual Science, Assoc. for Research in Vision and Ophthalmology, US, vol. 4, No. 5, Oct. 1, 1965.

Nesterov AP et al. "Surgical stimulation of the uveoscleral outflow. Experimental studies on enucleated human eyes" Acta Opthalmol (Copenh) June; 57(3):409-17 (1979).

Nguyen et al., "Complications of Baerveldt Glaucoma Drainage Implants" Arch Ophthal.; May 1998; vol. 116:571-575.

Noecker RJ. Clinical Evaluation of a Novel Gold Micro-Shunt for Reduction of 10 P in Refractory Glaucomas. American Glaucoma Society Annual Meeting, San Francisco, CA, 2007.http://www.glaucomaweb.org/associations/5224/files/AGS%20AM07%20Prgm%20FINAL.pdf. Accessed Nov. 1, 2008).

O'Brien et al. "Cyclodialysis" Arch Ophthal. 1949;42(5):606-619.

Odrich. "The New Technique During Complex Tube-Shunt Implantation". J. Glaucoma. vol. 9 No. 3 (2000):278-279.

Olsen, Timothy W., et al., Cannulation of the Suprachoroidal Space: A Novel Drug Delivery Methodology to the Posterior Segment, American Journal of Ophthalmology, vol. 142, No. 5, Nov. 2006, pp. 777-787.e2.

Ozdamar et al. "Suprachoroidal seton implantation in refractory glaucoma: a novel surgical technique" J. Glaucoma Aug. 2003; 12(4):354-9.

Pinnas G. et al. "Cyclodialysis with teflon tube implants" Am J. Ophthalmol Nov. 1969; 68(5):879-883.

Portney GL, "Silicone elastomer implantation cyclodialysis." Arch Ophthalmol 1973; 89: 10-12.

Primary Open Angle Glaucoma. Preferred Practice Patterns, American Academy of Ophthalmology.http://one.aao.org/CE/PracticeGuidelines/PPP_Content.aspx?cid=a5a59e02-450b-4d50-8091-b2dd2lefl ff2#references (Accessed Nov. 1, 2008).

Pruett et al., "The Fishmouth Phenomenon—II. Wedge Scleral Buckling" Arch Ophthal.; Oct. 1977; vol. 95:1782-1787.

Qadeer "Acrylic Gonio-Subconjunctival Plates in Glaucoma Surgery " Br J Ophthalmol. Jun. 1954; 38(6): 353-356.

Quigley HA, Vitale S. Models of open-angle glaucoma prevalence and incidence in the United States. Invest Ophthalmol Vis Sci 1997; 38:83-91.

Richards et al. "Artificial Drainage Tubes for Glaucoma" Am J Ophth 60:1965,405-408.

Ritch, et al., "Uveoscleral Outflow", The Glaucomas. St. Louis: Mosby, 1996; pp. 337-343.

Rohen, Johannes W., Anatomy of the Aqueous Outflow Channels, Glaucoma, vol. 1, Chapter 14, pp. 277-296, Edited by J.E. Cairns, Grune & Stratton, Harcourt Brace Jovanovich Publishers, 1986.

Rosenberg, et al. "Implants in glaucoma surgery" Chapter 88, The Glaucomas, Ritch et al. Eds. 2nd Ed. Mosby St. Louis 1996; p. 1783-1807.

Row H. "Operation to control glaucoma: preliminary report" Arch. Ophthal 12:325 (1934).

Rowan, Patrick J., MD, Combined Cyclodialysis and Cataract Surgery, Ophthalmic Surgery and Lasers, Dec. 1998, vol. 29, No. 12, pp. 962-968 (9 pages).

Sampimon "A New Approach to Filtering Glaucoma Surgery" Ophthalmologica (Basel) 151: 1966, 637-644.

Schappert S. Office visits for glaucoma: United States, 1991-92. Advance data from vital and health statistics. vol. 262. Hyattsville, MD: National Center for Health Statistics, 1995.

Schocket, Stanley S. "Investigations of the Reasons for Success and Failure in the Anterior Shunt-To-The-Encircling-Band Procedure in the Treatment of Refractory Glaucoma." Tr. Am. Ophth. Soc.vol. LXXXIX. (1986):743-798.

Shaffer RN, Weiss DI. Concerning cyclodialysis and hypotony. Arch Ophthalmol 68: 25, 1962.

SOLX Clinical Literature Handout; Industry Show Feb. 2006; "The SOLX Gold Micro-shunt (GMS) treatment".

Sommer A, Tielsch JM, Katz J, et al. Racial differences in the cause-specific prevalence of blindness in east Baltimore. n. Engl J Med 1991;325:1412-7.

Sourdille et al. "Reticulated hyaluronic acid implant in non-perforating trabecular surgery." J Cataract Refract Surg 25: 332-339. (1999).

Spiegel et al. "Schlemm's Canal Implant: A New Method to Lower Intraocular Pressure in Patients With POAG?" Ophthalmic Surgery and Lasers. vol. 30, No. 6: 492-494. Jun. 1999.

Srinivasan et al. "Microbial contamination of the anterior chamber during phacoemulsification" J. Cataract Refract Surg. 28:2173-6 (2002).

Suguro K, Toris CB, Pederson JE. Uveoscleral outflow following cyclodialysis in the monkey eye using a fluorescent tracer. Invest Ophthalmol Vis Sci 1985: 26, 810.

The Advanced Glaucoma Intervention Study (AGIS): 7. The relationship between control of intraocular pressure and visual field deterioration. The AGIS Investigators. Am J Ophthalmol 2000;130:429-40.

The Advanced Glaucoma Intervention Study (AGIS); 13. Comparison of treatment outcomes within race: 10-year results. Ophthalmology 2004;111:651-64.

The Glaucoma Laser Trial (GLT) and Glaucoma Laser Trial Follow-up Study: 7. Results. Am J Ophthahnol 1995;120:718-31.

The Glaucoma Laser Trial (GLT). 2. Results of argon laser trabeculoplasty versus topical medicines. The Glaucoma Laser Trial Research Group. Ophthalmology 1990;97:1403-13.

Thiagalingam S, Tarongoy P, Hamrah P, Lobo AM, Nagao K, Barsam C, Bellows R, Pineda R. Complications of cosmetic iris implants. J Cataract Refract Surg. Jul. 2008:34(7)1222-4.

Tielsch JM, Sommer A, Katz J, et al. Racial variations in the prevalence of primary open-angle glaucoma. The Baltimore Eye Survey. JAMA 1991;266:369-74.

Toris CB. Extravascular albumin concentration of the uvea. Invest Ophthalmol Vis Sci 1990; 31:43.

Toris et al. "Aqueous humor dynamics in the aging human eye" Am J. Ophthalmol., 127:407-12 (1999).

Toris et al. "Effect of intraocular pressure on uveoscleral outflow following cyclodialysis in the monkey eye." Investigative Ophthalmology & Visual Science. 26 (1985) 1745-1749.

Transcend Medical Inc. v. Glaukos Corporation, Transcend Medical, Inc.'s Disclosures Pursuant to Default Discovery Rule 4 (d) (United States District Court for the District of Delaware, dated Dec. 6, 2013; case No. C.A. No. 13-830 (MSG) and Certificate of Service, dated Dec. 9, 2013.

(56) References Cited

OTHER PUBLICATIONS

Trigler L, Proia AD, Freedman SF. Fibrovascular ingrowth as a cause of Ahmed glaucoma valve failure in children. Am J Ophthalmol. Feb. 2006;141(2):388-9.

Troncoso Manuel U., "Cyclodialysis with insertion of metal implant in treatment of glaucoma, A Preliminary Report" Arch. Ophthal. 23:270 (1940).

Troncoso, Manuel U., Tantalum implants for inducing hypotny, Am Journal of Ophthalmology, vol. 32(4):499-508 (1949).

Vossmerbaeumer U, Ditzen K, Jonas JB. Removal of an intracorneal hydrogel implant for hyperopia after Lasik. J Refract Surg. Jan. 2007;23(1):102-4.

Wagner, Justin A., et al., Characterization of Uveoscleral Outflow in Enucleated Porcine Eyes Perfused under Constant Pressure, Invest Ophthalmol Vis Sci., Published in edited form in Sep. 2004, vol. 45, Issue 9, pp. 3203-3206.

Wamsley S, Moster MR, Rai S, Alvim HS, Fontanarosa J. Results of the use of the Ex-Press miniature glaucoma implant in technically challenging, advanced glaucoma cases: a clinical pilot study. Am J Ophthalmol. Dec. 2004; 138(6): 1049-51.

Yablonski, "Some thoughts on the pressure dependence of uveoscleral flow" Journal of Glaucoma, 12(1):90-92 (2003).

Yablonski, "Trabeculectomy with Internal Tube Shunt: a novel glaucoma surgery" J. Glaucoma 14:91-97 (2005).

Yoo C, Kwon SW, Kim YY. Pericardium plug in the repair of the corneoscleral fistula after ahmed glaucoma valve explantation. Korean J Ophthalmol. Dec. 2008;22(4):268-71.

Zhou et al. "A trabecular bypass flow hypothesis" J Glaucoma. 14(1):74-83 (2005).

* cited by examiner

EXPANDING OCULAR IMPLANT DEVICES AND METHODS

REFERENCE TO PRIORITY DOCUMENT

This application claims the benefit of priority under 35 U.S.C. §119(e) of U.S. Provisional Patent Application Ser. No. 61/702,179 filed Sep. 17, 2012 under 37 C.F.R. §1.78 (a). Priority of the filing date is hereby claimed and the full disclosure of the aforementioned application is incorporated herein by reference.

FIELD

The subject matter described herein relates to embodiments of implants and methods for treating one or more physiological conditions of an eye.

BACKGROUND

The mechanisms that cause glaucoma are not completely known. It is known that glaucoma results in abnormally high pressure in the eye, which leads to optic nerve damage. Over time, the increased pressure can cause damage to the optic nerve, which can lead to blindness. Treatment strategies have focused on keeping the intraocular pressure down in order to preserve as much vision as possible over the remainder of the patient's life.

Pursuant to such strategies, one or more implants can be delivered into the eye for shunting fluid out of the anterior chamber in order to regulate pressure in the eye. Accurate placement of an implant in the angle of the eye is critical for the targeted effect of reducing intraocular pressure (IOP). Placing an implant too distally into the eye, such as too distally into the supraciliary space, may leave no portion of the implant remaining in the anterior chamber. This may inhibit aqueous outflow, as the fluid will not have a direct communication with the flow target location if there is no opening to the anterior chamber.

Conversely if the implant is placed too proximally in the supraciliary space such that a significant portion of the implant remains in the anterior chamber, damage to the corneal endothelium may result from implants that protrude upwards and touch the cornea. Implants placed too proximally may also touch the iris resulting in increased amounts of pigment dispersion in the eye, which can increase outflow resistance and intraocular pressure by clogging the trabecular meshwork. Therefore, at least correct placement of the implant is desired for a safety and a successful surgical outcome.

SUMMARY

Disclosed herein are devices and methods related to implants for treating one or more physiological conditions of the eye. Some embodiments disclosed herein include an expandable sheath that can have at least one expandable feature configured to form an expanded and a compact configuration with the at least one expandable feature extending from at least one of a proximal collar and a distal collar. In addition, the at least one of the proximal collar and distal collar can be adaptable to an ocular implant.

Some embodiments of methods disclosed herein include providing an expandable sheath, wherein the expandable sheath includes at least one expandable feature configured to form an expanded and a compact configuration. In addition, the at least one expandable feature can extend from at least one of a proximal collar and a distal collar, and the at least one of the proximal collar and distal collar can be adaptable to an ocular implant. Additionally, the method can further include adapting the expandable sheath to the implant and implanting the implant and the expandable sheath into an eye.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

These and other aspects will now be described in detail with reference to the following drawings.

Like reference symbols in the various drawings indicate like elements.

DETAILED DESCRIPTION

This disclosure describes embodiments of an expandable sheath that can be securely adapted to an ocular implant to form an expandable ocular implant, which can be implanted into the eye. The expandable sheath can include at least one expandable feature that can form a compact and expanded configuration. For example, the compact configuration can allow the expandable implant to be implanted into the eye without requiring a large incision, and the expanded configuration can assist in promoting fluid flow in the eye, such as for assisting in treating glaucoma.

Figure 1:
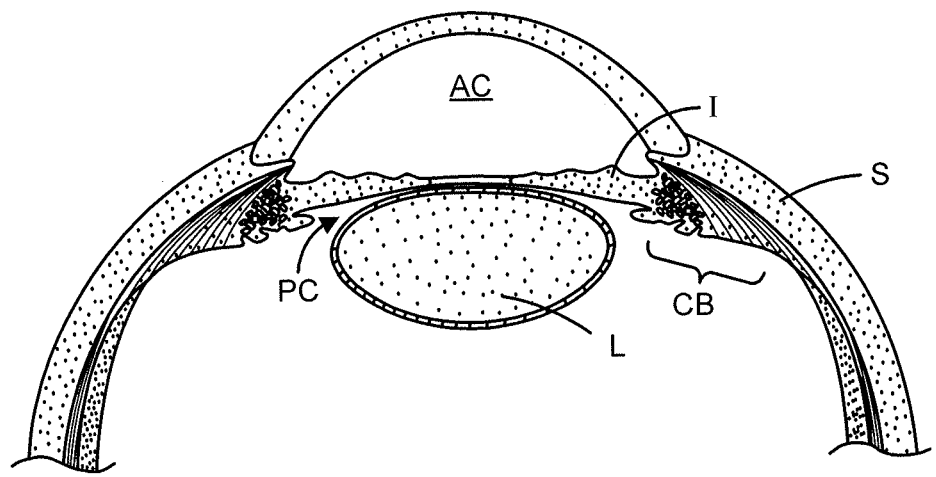
FIG. 1 shows an example cross-sectional view of a portion of the human eye.

FIG. 1 is a cross-sectional view of a portion of the human eye. The eye is generally spherical and is covered on the outside by the sclera S. The retina lines the inside posterior half of the eye. The retina registers the light and sends signals to the brain via the optic nerve. The bulk of the eye is filled and supported by the vitreous body, a clear, jelly-like substance. The elastic lens L is located near the front of the eye. The lens L provides adjustment of focus and is suspended within a capsular bag from the ciliary body CB, which contains the muscles that change the focal length of the lens. A volume in front of the lens L is divided into two by the iris I, which controls the aperture of the lens and the amount of light striking the retina. The pupil is a hole in the center of the iris I through which light passes. The volume between the iris I and the lens L is the posterior chamber PC. The volume between the iris I and the cornea is the anterior chamber AC. Both chambers are filled with a clear liquid known as aqueous humor.

The ciliary body CB continuously forms aqueous humor in the posterior chamber PC by secretion from the blood vessels. The aqueous humor flows around the lens L and iris I into the anterior chamber and exits the eye through the trabecular meshwork, a sieve-like structure situated at the corner of the iris I and the wall of the eye (the corner is known as the iridocorneal angle). Some of the aqueous humor can filter through the trabecular meshwork near the iris root into Schlemm's canal, a small channel that drains into the ocular veins. A smaller portion rejoins the venous circulation after passing through the ciliary body and eventually through the sclera (the uveoscleral route).

Figure 2:
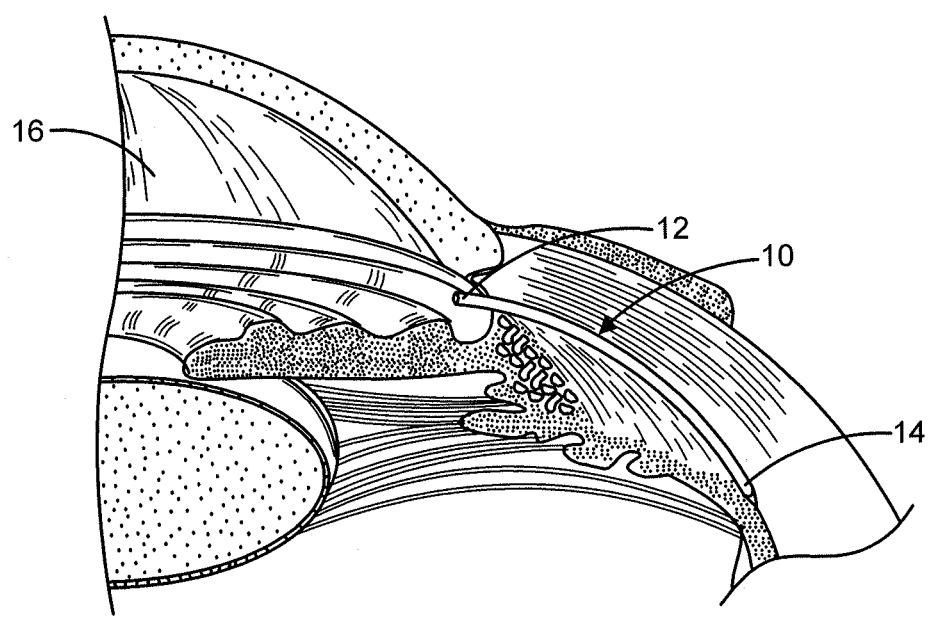
FIG. 2 shows and an example cross-sectional perspective view of a portion of the eye showing a part of the anterior and posterior chambers of the eye.

FIG. 2 is a cross-sectional, perspective view of a portion of the eye showing the anterior and posterior chambers of the eye. A schematic representation of an embodiment of an implant 10, such as an expandable implant, is shown positioned inside the eye such that a proximal end 12 is located in the anterior chamber 16 and a distal end 14 communicates with and/or is located in or near the suprachoroidal space. It should be appreciated that FIG. 1 and other figures herein are schematic and are not necessarily to scale with respect to size and relative positions of actual eye tissue.

The implant 10 can provide a fluid pathway between at least the anterior chamber 16 into the supraciliary space or the suprachoroidal space. For example, the implant 10 can include a distal end 14 that may be positioned in the supraciliary space or the suprachoroidal space. The implant 10 may be positioned at least partially between the ciliary body and the sclera or it may be at least partially positioned between the sclera and the choroid. However, the distal end 14 of the implant 10 may be positioned between other anatomical parts of the eye.

In some embodiments, the implant 10 can include an elongate tubular element having one or more internal lumens through which aqueous humor can flow from the anterior chamber 16 into the supraciliary space. The implant 10 can have a substantially uniform internal diameter along its entire length, although the shape of the implant 10 can vary, such as along its length (either before or after insertion of the implant). Moreover, the implant 10 can have various cross-sectional shapes (such as a, circular, oval or rectangular shape) and can vary in cross-sectional shape moving along its length. For example, the cross-sectional shape can be selected to facilitate easy insertion into the eye. The following applications describe exemplary implants: U.S. Patent Publication Nos. 2007-0191863 and 2009-0182421. These applications are incorporated by reference in their entirety.

The internal lumen of the implant 10 can serve as a passageway for the flow of aqueous humor through the implant 10 directly from the anterior chamber 16 toward or into the suprachoroidal space. In addition, the internal lumen of the implant can be used as an access location to mount the implant 10 onto a delivery system, as will be described in more detail below. The internal lumen can also be used as a pathway for flowing fluid, such as an irrigation fluid or a visco-elastic substance(s), into the eye for flushing or to maintain pressure in the anterior chamber, or using the fluid to assist in dissection, visualization or hydraulic creation of a dissection plane into or within the suprachoroidal space. Fluid can be flowed toward or into the suprachoroidal space, for example via a delivery cannula or through the internal lumen of the shunt. The fluid can be flowed into the eye with a pressure sufficient to form a dissection plane into or within the suprachoroidal space. The fluid can accumulate within the eye so as to form a lake. In general, hydro-dissection or the injection of fluids such as a visco-elastic substance(s) can be used to separate the ciliary body from the sclera to enlarge an area of detachment of the ciliary body from the sclera with or without insertion of a device.

In at least some instances, reduction in IOP can be correlated with the position of the implant 10 creating an area of separation between the choroid and sclera around at least a part of the implant 10 (also known as "tenting") and a space created around, for example, the most distal portion 14 of the implant 10 (also known as an "aqueous lake"). In addition, increasing the area of scleral and choroidal separation can improve IOP reduction in at least some instances.

Although increasing the area of scleral and choroidal separation can be advantageous, several drawbacks may occur if a lager implant 10, such as an implant larger than approximately 0.5-1.0 mm in diameter, is used to create the larger separation. For example, some drawbacks may include the requirement for a larger incision, such as along the limbus, due to a greater diameter implant 10. A larger incision may cause fluids to escape the eye, such as at least from the anterior chamber, and complicate the implantation procedure. For example, an incision less than approximately 2.5 mm may be preferable for implantation of at least one implant 10.

Other drawbacks to using a larger diameter implant 10 can include creating a larger cyclodialysis which may result in increased rates of hypotony post operatively and increased rates of retinal detachments. In addition, a larger implant 10 can be more difficult to insert into the supracilliary and suprachoroidal space due to the requirement of greater tissue separation which may result in excess tissue damage. Therefore, an implant 10 that can maintain a compact configuration during implantation and then form an expanded configuration once implanted may overcome the drawbacks discussed above while achieving increased separation between the sclera and choroid for an improved reduction in IOP.

The present disclosure includes various embodiments of expandable sheaths that can be functionally coupled to one or more implants 10 and can function by providing a compact configuration during implantation of the implant and form an expanded configuration once implanted in a patient's eye. Some embodiments disclosed herein include implants having expanding features that function similar to an expanding sheath such that these expanding features can maintain a compact configuration during implantation and expand once the implant has been implanted in the patient's eye.

Figure 3:
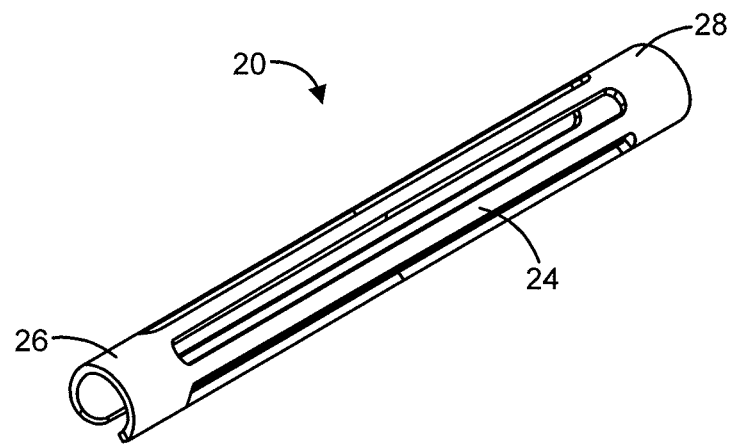
FIG. 3 illustrates an embodiment of an expandable sheath in a compact configuration which may be used in combination with one or more ocular implants to form an expandable implant.
Figure 4:
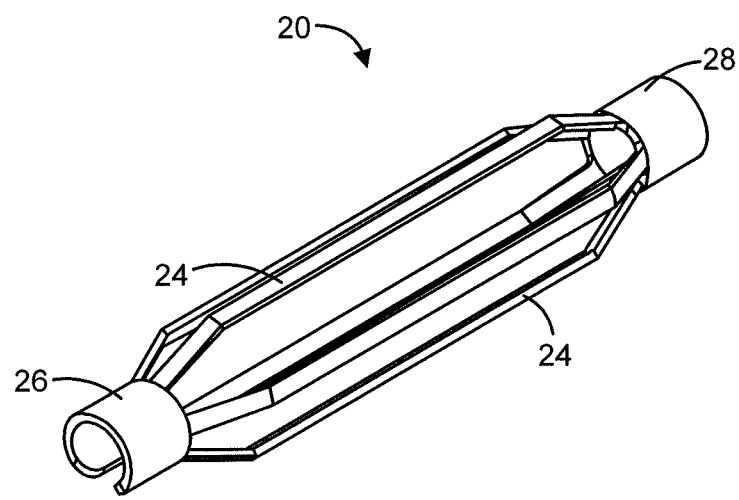
FIG. 4 illustrates an embodiment of an expandable sheath in an expanded configuration which may be used in combination with one or more ocular implants to form an expandable implant.
Figure 5:
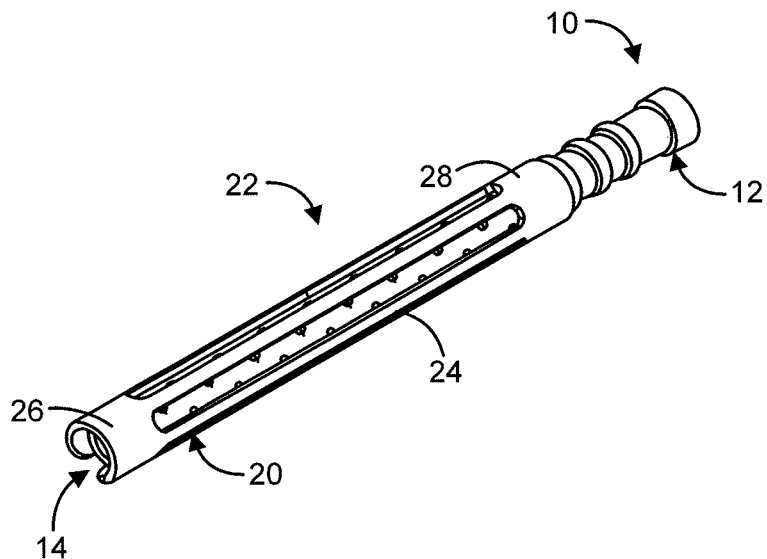
FIG. 5 illustrates an embodiment of an expandable implant in a compact configuration.
Figure 6:
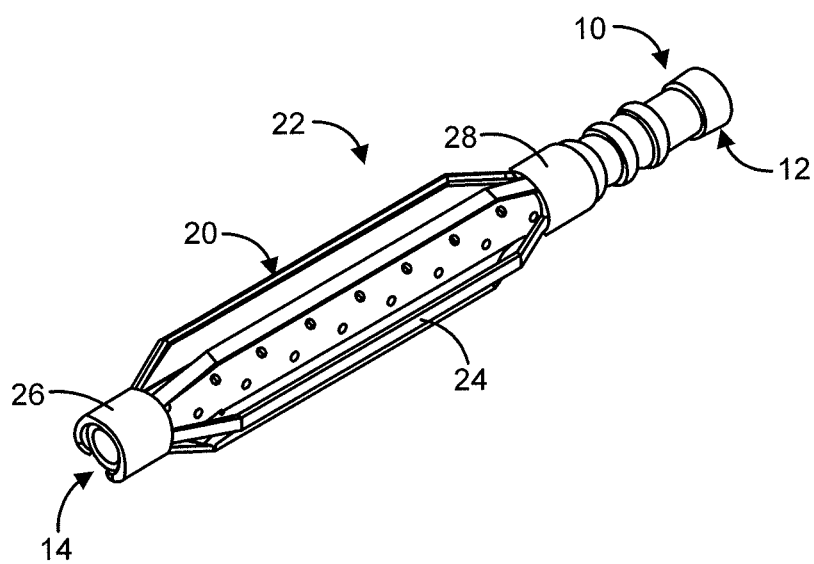
FIG. 6 illustrates an embodiment of an expandable implant in an expanded configuration.

FIGS. 3 and 4 illustrate an embodiment of an expandable sheath 20 which may be used in combination with one or more ocular implants, such as the implant 10 discussed above, to form an expandable implant 22 (as shown in FIGS. 5 and 6). The expandable sheath 20 can include one or more expandable features 24, such as struts, that extend between a distal collar 26 and a proximal collar 28. At least one of the distal collar 26 or proximal collar 28 can be used to couple the expandable sheath 20 to an implant 10. The expandable sheath 20 can be made from any number of medical grade materials that allow the expandable sheath to form a condensed configuration during implantation, as shown for example in FIG. 3, and an expanded configuration, as shown for example in FIG. 4.

FIGS. 5 and 6 illustrate an embodiment of an expandable implant 22 in a condensed and expanded configuration, respectively. The expandable implant 22 can include the expandable sheath 20 functionally coupled or securely adapted to the implant 10 such that the expandable sheath 20 can form at least a compact and expanded configuration. Some embodiments of the expandable sheath 20 may be coupled to the implant 10 such that the expandable sheath 20 can form a compact and expanded configuration without generally disrupting the shape of the implant 10.

In an embodiment of the expandable implant 22, the proximal collar 28 of the expandable sheath 20 can secure to at least a part of the proximal end 12 of the implant 10. The proximal collar 28 may be secured to the implant 10 such that the proximal collar 28 is permanently fixed and may not move relative to the implant 10. In addition, the distal collar 26 of the expandable sheath 20 may be coupled to at least part of the distal end 14 of the implant 10 such that the distal collar 26 may be movable relative to the implant 10. In this configuration, the distal collar 26 may be allowed to slide along at least a part of the distal end 14 of the implant 10 during deformation of the expandable sheath 20, such as from a compact to an expanded shape. By permanently fixing only one end of the expandable sheath 20, such as the proximal collar 28, to the implant 10 the shape of the implant 10 may not be affected during, for example, expansion of the expandable sheath 20.

One or more restraints (not shown) may be used to assist the expandable sheath 20 in maintaining a compact configuration, such as during implantation. In addition, the one or more restraints may be releasable in order to allow the expandable sheath 20 to deform into an expanded configuration. Any number of restraints may be used that can assist in maintaining the expandable sheath 20 in a compact configuration while also allowing at least the expandable sheath 20 to maintain a small diameter, such as less than approximately 2.5 mm. For example, a tubing having an inner diameter that is larger than or equal to the outer diameter of the expandable sheath 20 or expandable features 24 in a compact configuration may be used to restrain expandable features 24 in a compact configuration. However, any number of features or mechanisms can be coupled with the expandable implant 22 to assist in restraining the expandable features 24 in a compact configuration until expansion is desired without departing from this disclosure.

For example, the expandable sheath 20 may be coupled to the implant 10 and restrained in a compact configuration such that the expandable implant 22 can have a minimal outer diameter. The expandable sheath 20 can maintain the condensed configuration around the implant during implantation of the expandable implant 22, such as with the use of a restraint. Once the expandable implant 22 has been positioned in the target implantation site in the eye, the restraint can be released to allow the expandable sheath 20 to deform into an expanded configuration, as shown for example in FIG. 6. As discussed above, the expandable sheath 20 can be made out of a shape memory material which can assist in deforming the expandable sheath from a compact to an expanded configuration once the restraint is released.

The one or more expandable features 24, such as the struts shown in FIGS. 3-6, can extend between the proximal collar 28 and distal collar 26 and can assist in allowing the expandable sheath 20 to form a condensed and expanded configuration. For example, the struts 24 may deform from an expanded configuration, as shown in FIG. 6. In the expanded configuration, the expandable features 24 can assist in separating surrounding tissue. For example, positioning at least part of the expandable sheath 20 between a part of the sclera and choroid and allowing the expandable features 24 to form an expanded configuration, the expandable sheath 20 can assist in increasing the separation between the choroid and sclera. The expandable features 24 can assist in separating the choroid and sclera while also allowing fluids to at least pass through the expandable features 24, thus allowing fluid flow through at least the expandable sheath 20.

Figure 7:
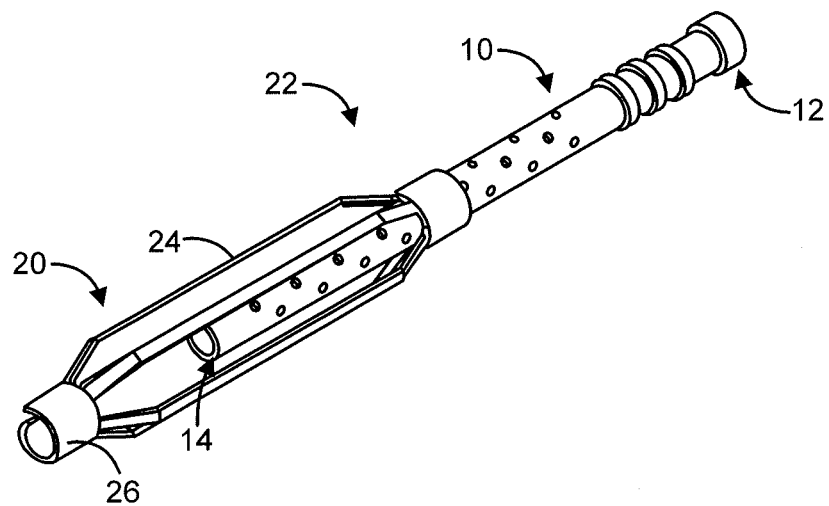
FIG. 7 illustrates an embodiment of an expandable sheath with the proximal collar coupled to the implant in a more distal position.

FIG. 7 illustrates an embodiment of an expandable sheath 20 with the proximal collar 28 coupled to the implant 10 in a more distal position. In this configuration, the distal collar 26 of the expandable sheath 20 can extend more distally than the distal end 14 of the implant 10. In general, the expandable sheath 20 can be functionally coupled to the implant 10 in any number of ways, and either the proximal collar 28 or distal collar 26 can be in permanent fixed relation to the implant 10 or may be movable relative to the implant 10. The expandable sheath 20 may include a variety of shaped and sized expandable features 24 for assisting in forming an expanded configuration, as will be discussed in greater detail below.

Figure 8:
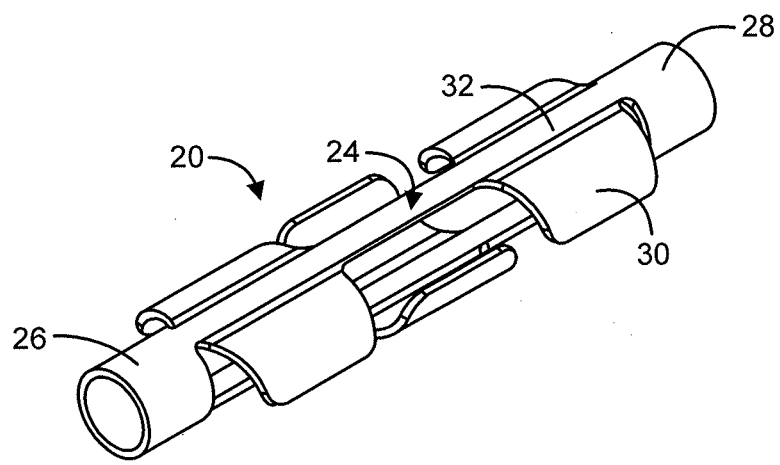
FIG. 8 illustrates an embodiment of an expandable sheath having expandable features which include one or more wings extending from at least one support.

FIG. 8 illustrates an embodiment of an expandable sheath having expandable features 24 including one or more wings 30 extending from at least one support 32. A restraint can be used for restraining the wings 30 in a compact configuration, such as during implantation. Release of the restraint can allow the expandable sheath 20 to form an expanded configuration, as shown in FIG. 8. In an expanded configuration, the wings 30 can extend radially and assist in further separating tissue, such as between the sclera and choroid. Similar to expandable sheath 20 embodiments discussed above, at least a part of the expandable features 24 can be made out of medical grade shape memory material so that upon release of the restraint at least the wings 30 can deform to an expanded configuration.

Figure 9:
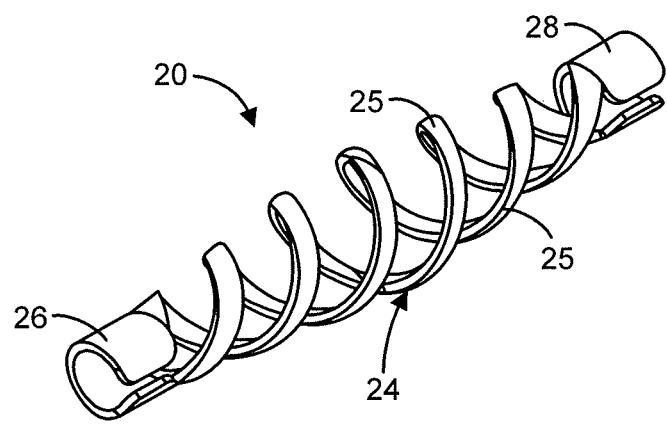
FIG. 9 illustrates an embodiment of an expandable sheath having expandable features which include at least one helical support that extends between the proximal collar and distal collar.

FIG. 9 illustrates an embodiment of an expandable sheath 20 having expandable features 24 which include at least one helical support 25 that extends between the proximal collar 28 and distal collar 26. The helical supports 25 may form a condensed configuration with a minimal diameter around the implant 10, such as during implantation. In addition, the helical supports 25 can deform and expand such that the outer diameter of the helix formed by the helical supports 25 increases. A restraint may also be used, such as those described above, for restraining the helical supports 25 in a compact configuration during implantation. Release of the restraint, such as once the expandable implant 22 is positioned within a patient's eye, can allow the expandable sheath 20 to form an expanded configuration, as shown in FIG. 9. In an expanded configuration, the helical supports 25 may assist in further separating tissue, such as between the sclera and choroid.

Figure 10:
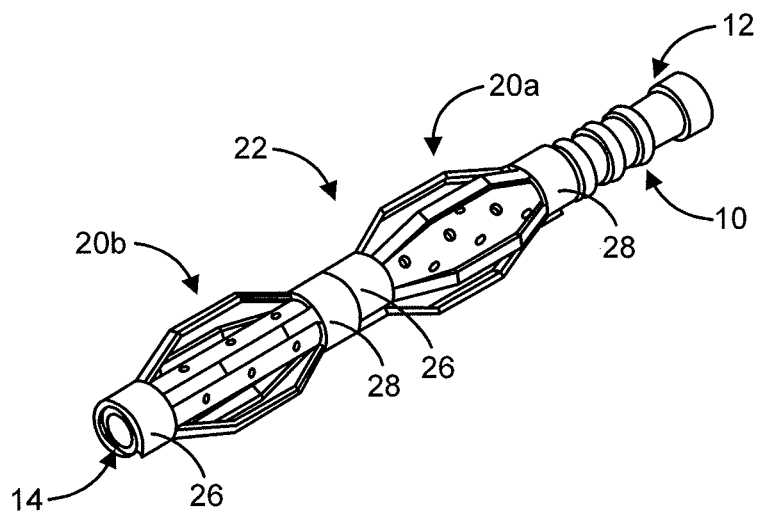
FIG. 10 illustrates an embodiment of an expandable implant that is configured to form more than one expanding area.

FIG. 10 illustrates an embodiment of an expandable implant 22 that is configured to form more than one expanding area. The expandable implant 22 shown in FIG. 10 may be comprised of two expandable sheaths 20a and 20b coupled consecutively along the length of the implant 10. The more than one expanding area may be formed by coupling more than one expandable sheath 20 along an implant 10 or a single expandable sheath 20 may be configured to form more than one expanding area.

One or more restraints can be used to constrain the expandable features 24 of the expandable sheaths 20a and 20b. It may be possible to release the one or more restraints such that the expandable sheaths 20a and 20b are allowed to expand independently or in unison. In addition, any one of the proximal collars 28 or distal collars 26 of the expandable sheaths 20a and 20b may be permanently fixed relative to the implant 10 or movable relative to the implant 10.

Figure 11:
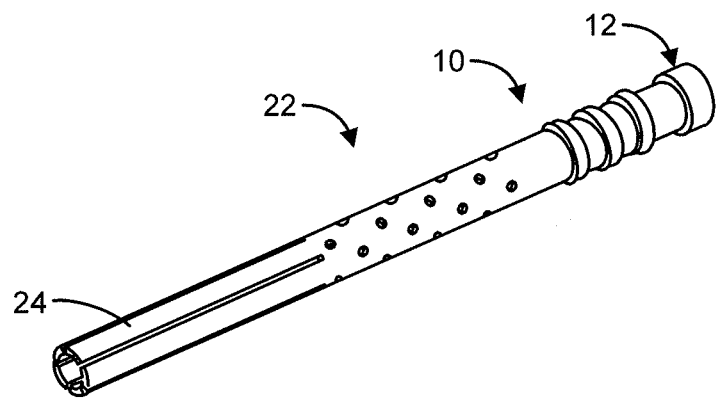
FIG. 11 illustrates an embodiment of an expandable implant having one or more expandable features extending in a compact configuration from the distal end of the implant.
Figure 12:
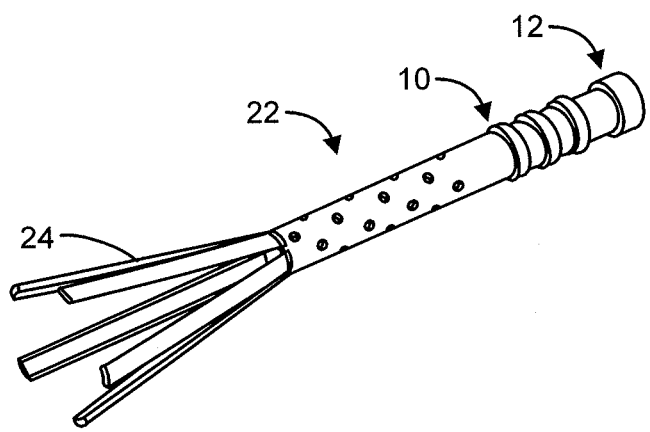
FIG. 12 illustrates an embodiment of an expandable implant having one or more expandable features extending in an expanded configuration from the distal end of the implant.

FIGS. 11 and 12 illustrate an embodiment of an expandable implant 22 having one or more expandable features 24 extending from the distal end of the implant 10. In this configuration, the expandable features 24 may be part of the implant 10 instead of part of an expandable sheath that is functionally coupled to the implant 10. The expandable features 24 can include extensions which may form a condensed configuration, as shown for example in FIG. 11, and flare out into an expanded configuration, as shown for example in FIG. 12. In this configuration, the expandable implant may be able to achieve a smaller compact diameter due to the expandable features 24 extending distally from the implant instead of alongside the implant 10, as shown for example in FIG. 5.

Similar to other expandable implants 22 described herein, the expandable features 24 can be made out of a medical grade shape memory material such that upon release of a restraint, the expandable features 24 may deform into an expanded configuration. One or more restraints may also be used for restraining the expandable features 24 in a compact configuration during implantation. Release of the restraints can allow the extensions to form an expanded configuration, as shown in FIG. 12. In an expanded configuration, the extensions may assist in further separating tissue, such as between the sclera and choroid.

Figure 13:
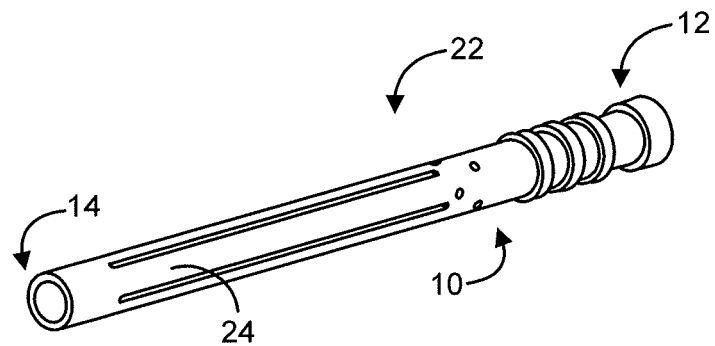
FIG. 13 illustrates another embodiment of an expandable implant having at least one expandable feature in a compact configuration extending between the distal end and proximal end of the implant.
Figure 14:
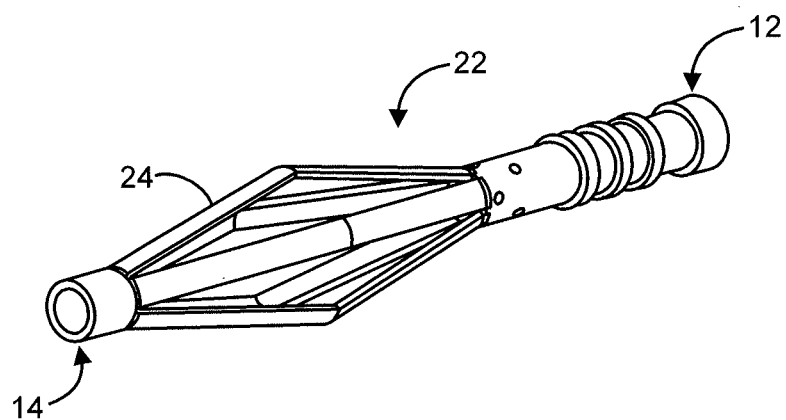
FIG. 14 illustrates an embodiment of an expandable implant having at least one expandable feature in an expanded configuration extending between the distal end and proximal end of the implant.

FIGS. 13 and 14 illustrate another embodiment of an expandable implant 22 having at least one expandable feature 24 extending between the distal end 14 and proximal end 12 of the implant 10. In this configuration, the expandable features 24 may be part of the implant 10 instead of part of an expandable sheath that is functionally coupled to the implant 10. The expandable features 24 can include extensions or struts which may form a condensed configuration, as shown for example in FIG. 13, and expand radially into an expanded configuration, as shown for example in FIG. 14. This embodiment of the expandable implant 22 may be able to achieve a smaller compact diameter due to the expandable features 24 extending between the distal end 14 and proximal end 12 of the implant 10 instead of alongside the implant 10, as shown for example in FIG. 5.

Similar to other expandable implants 22 described herein, the expandable features 24 in FIGS. 13 and 14 can be made out of a medical grade shape memory material such that upon release of a restraint, the expandable features 24 may deform into an expanded configuration. One or more restraints may also be used for restraining the expandable features 24 in a compact configuration during implantation. Release of the restraints can allow the extensions to form an expanded configuration, as shown in FIG. 14. In an expanded configuration, the extensions may assist in further separating tissue, such as the sclera and choroid.

In general, the expandable features 24 can have any number of suitable shapes or patterns that can provide both a compact and expanded configuration for assisting in further separating tissue in an eye, such as between the sclera and choroid. In addition, any of the expandable features 24 at least described herein may be a part of the implant 10 or can be part of an expandable sheath 20 that is functionally coupled to the implant 10 without departing from the scope of this disclosure.

In addition, at least the expandable sheath 20 can be made out of any number of medical grade materials, including at least one of shape memory alloys, such as nitinol, or shape memory polymers. However, any number of medical grade materials may be used that allow the expandable sheath 20 to form a compact, or condensed, and expanded configuration. In addition, the expandable sheath 10 can be functionally coupled to the implant 10 in any number of ways, such as medical grade adhesive, heat shrink tubing, or various mechanical coupling. Furthermore, the expandable sheath may be functionally coupled to the implant in any number of ways that allow the expandable sheath to form at least a compact and expanded configuration.

The features and profile of the expandable sheath 20 may be formed by a variety of manufacturing methods. For example, the profile of the expandable sheath 20 may be laser cut or stamped from a flat sheet of material, such as a shape memory alloy, and rolled into a tubular shape that can functionally couple to an implant 10.

Figures 15A, 15B:
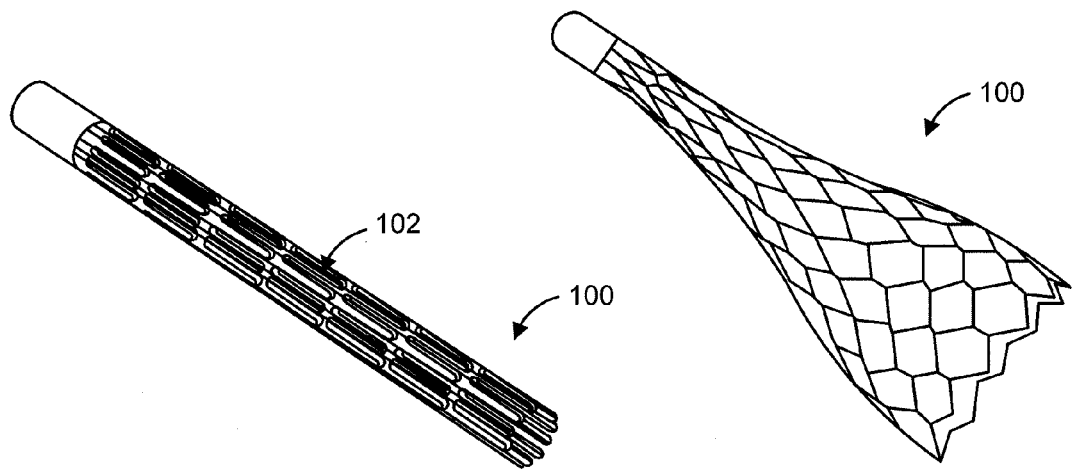
FIG. 15A illustrates an embodiment of a laser cut expandable sheath in a compact configuration.
FIG. 15B illustrates the laser cut expandable sheath shown in FIG. 15A in an expanded configuration

FIGS. 15A and 15B illustrate an embodiment of an expandable sheath 100 formed by laser cutting a medical grade material, including medical grade shape memory alloys, such as nitinol, and shape memory polymers. In addition, either a tube shape or a formable flat sheet of material made out of the medical grade material can be used. The shape of the expandable sheath 100 in its expanded configuration, as shown for example in FIG. 15B, may be defined in a shape setting operation, such as those operations used for shape memory alloys and polymers. For example, the expandable features 102 may be held radially open in an expanded configuration with the use of an internal mandrel or fixture during the shape setting operation.

Any number of expanded configurations have been contemplated, including full and partial expansion of the expandable sheath 100 after placement in the eye. In addition, any number of shapes and dimensions of both the compact and expanded configuration have been contemplated. For example, the expandable sheath 100 can have a compact configuration with an outside diameter dimension in the range of 0.4 millimeter to 0.6 millimeter, such as 0.5 millimeters. Additionally, the expandable sheath 100 can have an expanded configuration with an outside diameter dimension in the range of 2.0 millimeters to 3.0 millimeters, such as 2.5 millimeters.

In addition, some embodiments of the implant may include a body having a tube shaped configuration that is made out of a soft biocompatible material, such as silicone. When implanted in the eye, the tube shaped body may extend proximally out of the expandable sheath into the anterior chamber while the distal end of the tube may terminate approximately in the middle of the expandable sheath.

Additionally, at least a part of a surface of the expandable sheath 20 can be treated with one or more surface treatments that can modify the topography of the expandable sheath. For example, surface areas of the expandable sheath that have been treated with a surface treatment can cause a variety of ocular tissue responses as a result of the expandable sheath being implanted in the eye and contacting the treated surface area to the ocular tissue.

Any number of surface treatments can be applied to any part of the expandable sheath for assisting in creating a variety of ocular tissue responses. For example, a plasma cleaning process can be used to treat at least a part of the surface of the expandable sheath. In addition, one or more variables, such as power, processing time, and pressure, can be varied, including varying the power by approximately 250%, in order to achieve a desired surface topography.

Figure 16:
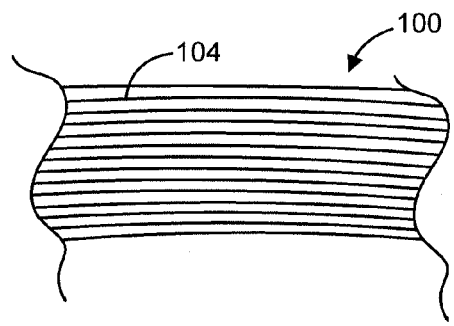
FIG. 16 illustrates a laser ablation treated surface of a part of the expandable sheath showing a micro-ribbed surface.

FIG. 16 illustrates an embodiment of a laser ablation pattern 104 applied to at least a part of the surface of the expandable sheath 100. For example, as shown in FIG. 16, the laser ablation pattern 104 can include at least one ribbed feature, including multiple micro ribs. Such laser ablation patterns 104 can provide a variety of tissue responses, and by varying at least one of the size and shape of the laser ablation patterns 104 any number of tissue responses can be achieved.

In addition, either the expandable sheath or implant can at least partially include at least one drug, such as either impregnated or coated with at least one drug. For example, at least the expandable sheath can include mitomycin or 5-FU, which can assist in reducing fibrotic and inflammatory tissue response, such as during trabeculectomy surgeries. Alternatively or in addition, the one or more drugs may be combined with a polymer comprising at least a part of either the expandable sheath or implant that can provide a sustained drug release profile during implantation of either the expandable sheath or implant.

In some embodiments of the expandable implant, the expandable sheath may include at least one drug, such as any drug described herein, while the implant, such as the implant having a tube shaped body, may not include a drug. Additionally, some embodiments of the expandable sheath can be implanted in the eye without being coupled to an implant.

In addition, a delivery system can be used to deliver an expandable implant 22 into the eye, for example such that the expandable implant 22 at least provides fluid communication between the anterior chamber toward the suprachoroidal space. As described above, the expandable implant 22 can include one or more expandable features 24 which may assist in further separating tissue, such as between the sclera and choroid.

Figure 17:
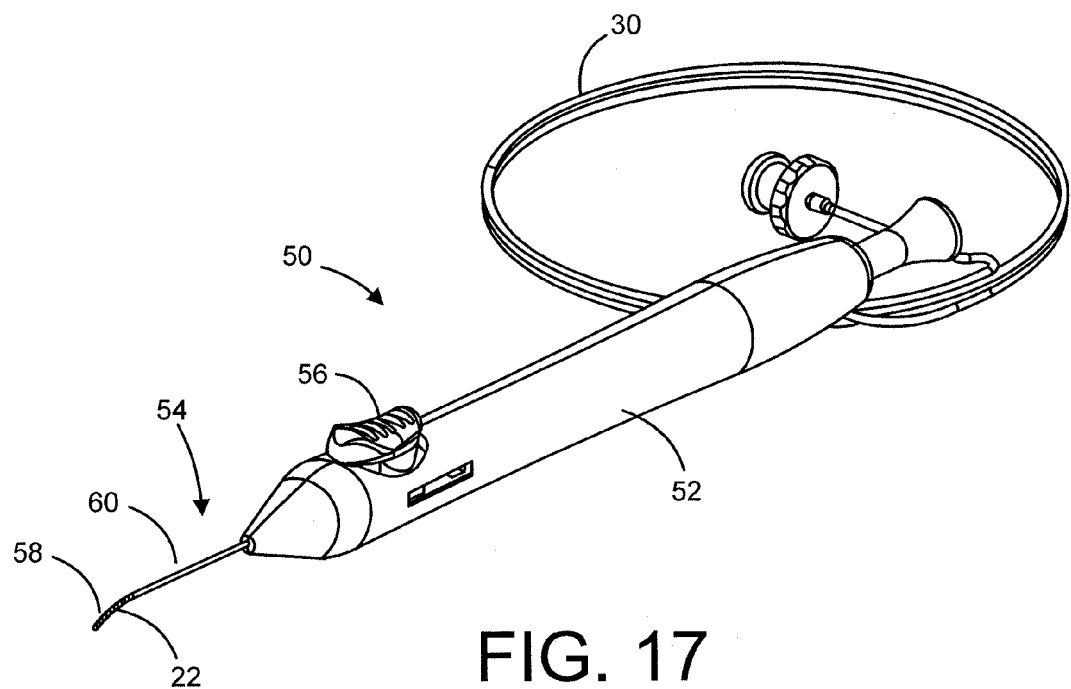
FIG. 17 shows an embodiment of a delivery system that can be used to deliver the expandable implant into the eye.

FIG. 17 shows an embodiment of a delivery system 50 that can be used to deliver the expandable implant 22 into the eye. It should be appreciated that these delivery systems 50 are exemplary and that variations in the structure, shape and actuation of the delivery system 50 are possible.

The delivery system 50 generally includes a proximal handle component 52 and a distal delivery component 54. The proximal handle component 52 can include an actuator 56, such as a button, to control the release of an expandable implant 22 from the delivery component 54 into the target location in the eye. The actuator 56 can vary in structure.

An embodiment of the delivery component 54 can include an elongate applier in the form of a guidewire 58 that inserts longitudinally through an internal lumen of the expandable implant 22 and a "stopper" or sheath 60 positioned axially over the guidewire 58. The sheath 60 can aid in the release of the expandable implant 22 from the delivery component 54 into the target location in the eye. The actuator 56 can be used to control movement or relative movement of the guidewire 58 and/or the sheath 60. For example, the sheath 60 can be fixed relative to the handle component 52 and act as a stopper that impedes the expandable implant 22 from moving in a proximal direction as the guidewire 58 is withdrawn proximally from the expandable implant 22 upon actuation of the actuator 56. In a first state, the guidewire 58 can be extended distally relative to the sheath 60. Actuation of the actuator 56, such as by pressing the actuator 56, can cause the guidewire 58 to slide proximally into the sheath 60. This can effectively disengage the expandable implant 22 off the distal end of the guidewire 58 and releases the expandable implant 22 in a controlled fashion such that the target positioning of the expandable implant 22 is maintained.

Figure 18:
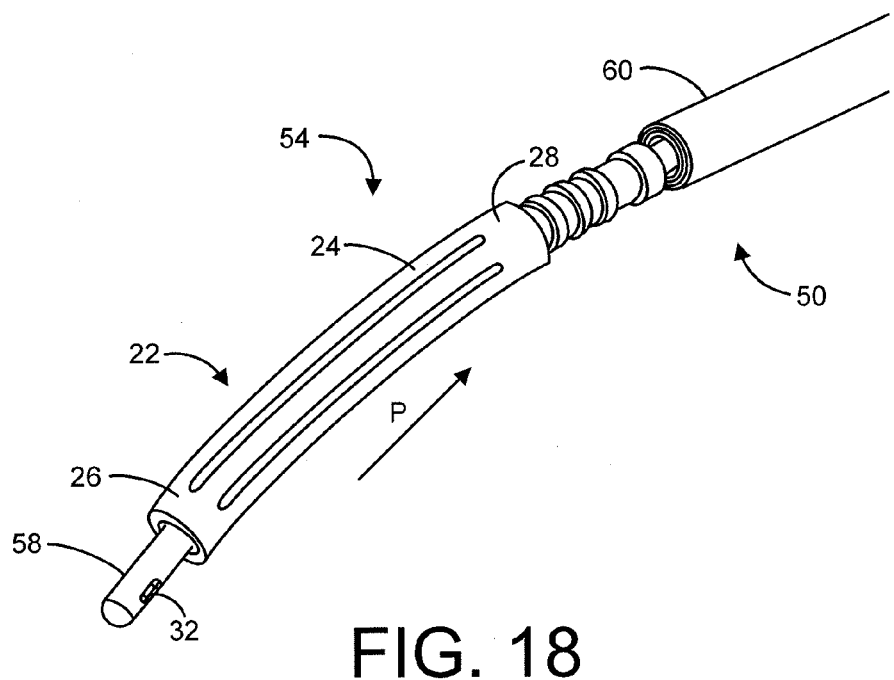
FIG. 18 shows an enlarged view of an expandable implant mounted on a delivery component for inserting the expandable implant into the eye.

FIG. 18 shows an enlarged view of an expandable implant 22 mounted on a delivery component 54 for inserting the expandable implant 22 into the eye. The expandable implant 22 can be mounted on a distal region of a guidewire 58. The sheath 60 can be sized and shaped to receive or abut a portion of the proximal end of the expandable implant 22. In this embodiment upon actuation of the actuator 56, the guidewire 58 can slide in the proximal direction (arrow P) into the sheath 60. The proximal end of the expandable implant 22 can abut the distal edge of the sheath 60 to prevent the expandable implant 22 from sliding in the proximal direction. This can effectively disengage the implant 10 off the distal end of the guidewire 58 and controllably release the expandable implant 22 into the eye tissue.

The delivery system 50 can also assist in providing fluid delivery into the eye during or after implantation of the expandable implant 22. The delivered fluid may vary and may include a viscoelastic, drugs, stem cells, or a combination thereof. The delivery may be in combination with retinal or macula therapy. A fluid delivery feature can include an elongated tube 30 that extends outward from the handle 52. The tube 30 can extend through the handle 52 and can have an internal lumen that communicates at a distal end with the proximal end of an internal lumen in the guidewire 58. One or more outlet openings, such as slots 32, can be located on the distal region of the guidewire 58. The tube 30 can be connected at a proximal end to a source of fluid so as to provide a pathway for the fluid to be delivered to the internal lumen of the guidewire via the tube 30. The fluid can then exit the guidewire via the slots 32 for delivery into the eye.

In alternate embodiments the fluid may be delivered to other sections along the axial length of the expandable implant 22. Holes along the length of the expandable implant 22 may be configured to be sufficiently large such that a fluid may be delivered through corresponding holes along the guidewire 58 and into the eye, such as into the supraciliary or suprachoroidal space surrounding the body of the expandable implant 22 (depending on where the implant is positioned and the length of the implant). This would be advantageous because it may create additional space surrounding the expandable implant 22 and improve tenting.

A method of delivering and implanting the expandable implant 22 into the eye is now described. In general, one or more expandable implants 22 can be slideably loaded on a delivery system 50 and implanted to a position that communicates with the suprachoroidal space as described herein. The expandable implant 22 can then be implanted in the eye via an ab-interno procedure through a limbal incision into the anterior chamber. The expandable implant 22 may then be secured in the eye so that it provides fluid communication between the anterior chamber and the suprachoroidal space, as well as provide increased separation between the sclera and choroid.

For example, the guidewire 58 can be positioned on the delivery system 50 such that the distal tip of the guidewire 58, the expandable implant 22 and the sheath 60 can penetrate through a small corneal incision and access the anterior chamber, such as within the limbus of the cornea. In an embodiment, the incision is very close to the limbus, such as either at the level of the limbus or within 2 mm of the limbus in the clear cornea. The guidewire 58 can be used to make the incision or a separate cutting device can be used. For example, a knife-tipped device or diamond knife can be used to initially enter the cornea.

The corneal incision can have a size that is sufficient to permit at least the passage of the expandable implant 22 on the guidewire 58 and sheath therethrough. In an embodiment, the incision can be about 1 mm in size. In another embodiment, the incision is no greater than about 2.5 mm in size. In another embodiment, the incision is no greater than about 2.85 mm and is greater than about 1.5 mm.

After insertion through the incision, the guidewire 58 can be advanced into the anterior chamber along a pathway that enables the expandable implant 22 to be delivered to a position such that the expandable implant 22 provides a flow passageway from the anterior chamber AC toward the suprachoroidal space. The guidewire 58 can be advanced further into the eye such that the blunt distal tip of the guidewire 58 and/or the expandable implant 22 can seat with and penetrate the iris root IR, or a region of the ciliary body CB, or the iris root part of the ciliary body near its tissue border with the scleral spur.

The guidewire 58 can approach the iris root from the same side of the anterior chamber AC as the deployment location such that the guidewire 58 does not have to be advanced across the iris. Alternately, the guidewire 58 can approach the location from across the anterior chamber AC such that the guidewire 58 is advanced across the iris and/or the anterior chamber toward the opposite iris root. The guidewire 58 can approach the eye and the iris root IR along a variety of pathways. The guidewire 58 does not necessarily cross over the eye and does not intersect the optical axis of the eye. In other words, the corneal incision and the location where the implant is implanted at the iris root can be in the same quadrant (if the eye is viewed from the front and divided into four quadrants). Also, the pathway of the implant from the corneal incision to the iris root desirably does not pass through the optic axis of the eye to avoid interfering with the pupil.

Figure 19:
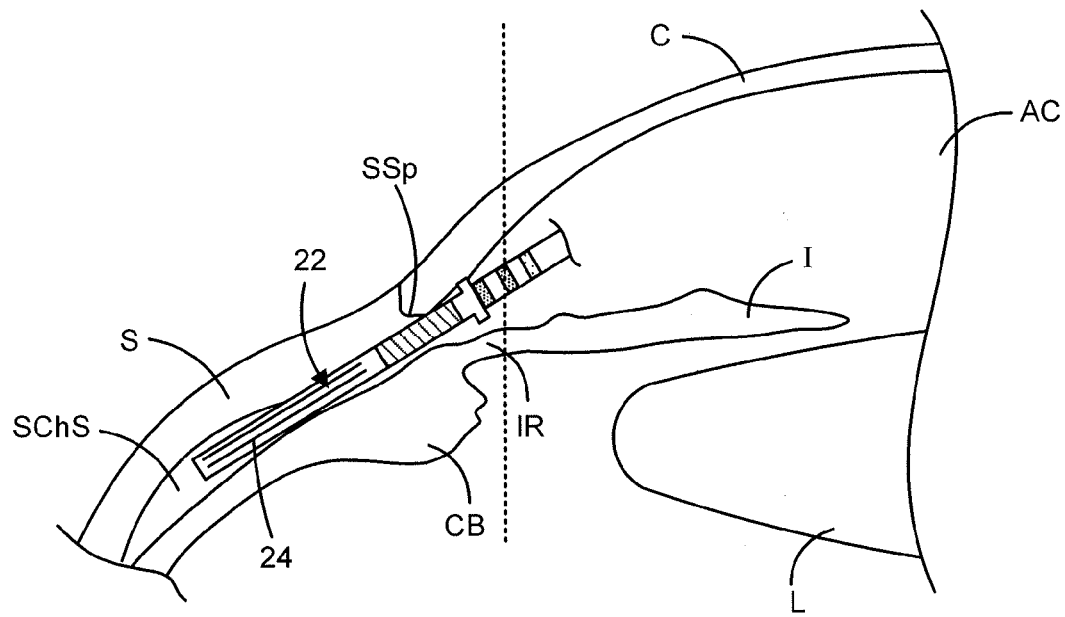
FIG. 19 shows an example of at least a part of the expandable features of the expandable implant positioned in the suprachoroidal space with the expandable features in a compact configuration.

FIG. 19 shows an enlarged view of the anterior region of the eye showing the anterior chamber AC, the cornea C, the iris I, and the sclera S. The expandable implant 22 mounted on the guidewire 58 can approach from the anterior chamber AC. The expandable implant 22 and guidewire 58 can move along a pathway such that the dissection entry point of the distal tip of the guidewire 58 can penetrate the iris root IR near its junction with the scleral spur SSp or the iris root portion of the ciliary body CB or other desired location. The surgeon can rotate or reposition the handle of the delivery device 50 in order to obtain a proper approach trajectory for the distal tip of the guidewire 58, as described in further detail below.

The guidewire 58 with the expandable implant 22 positioned thereupon can be advanced from a region of the anterior chamber that can be viewed through a transparent zone of the cornea through to a region of the anterior chamber that is obscured by the opaque zone of the cornea. The guidewire 58 and expandable implant 22 can be advanced through the cornea C until resistance is felt and the delivery device can be seated at a location near the iris root IR, the ciliary body or the iris root portion of the ciliary body. The guidewire 58 can then be advanced further such that the guidewire 58 and expandable implant 22 loaded thereon penetrate an area of fibrous attachment between the scleral spur SSP and the ciliary body CB. This area of fibrous attachment can be approximately 1 mm.

Once the distal tip of the guidewire 58 penetrates and is urged past this fibrous attachment region, the guidewire 58 can then more easily cause the sclera S to peel away or otherwise separate from the ciliary body CB and possibly the choroid as it follows the inner curve of the sclera S and enters the supraciliary space. A combination of the guidewire's tip shape, material, material properties, diameter, flexibility, compliance, coatings, pre-curvature etc. make it more inclined to follow an implantation pathway that mirrors the curvature of the inner wall of the sclera and between tissue layers such as between the sclera and the ciliary body, and between the sclera and the choroid.

The dissection plane of the guidewire 58 and expandable implant 22 can follow the curve of the inner scleral wall such that the expandable implant 22 mounted on the guidewire 58 after penetrating the iris root or the iris root portion of the ciliary body, bluntly dissects the boundary between tissue layers of the scleral spur SSp and the ciliary body CB such that at least the distal region of the expandable implant 22 extends into the supraciliary space. In an embodiment, the expandable implant 22 is positioned such that it extends sufficiently past the scleral spur SSP such that it is positioned between the tissue boundaries of the sclera and the choroid (the suprachoroidal space).

Figure 20:
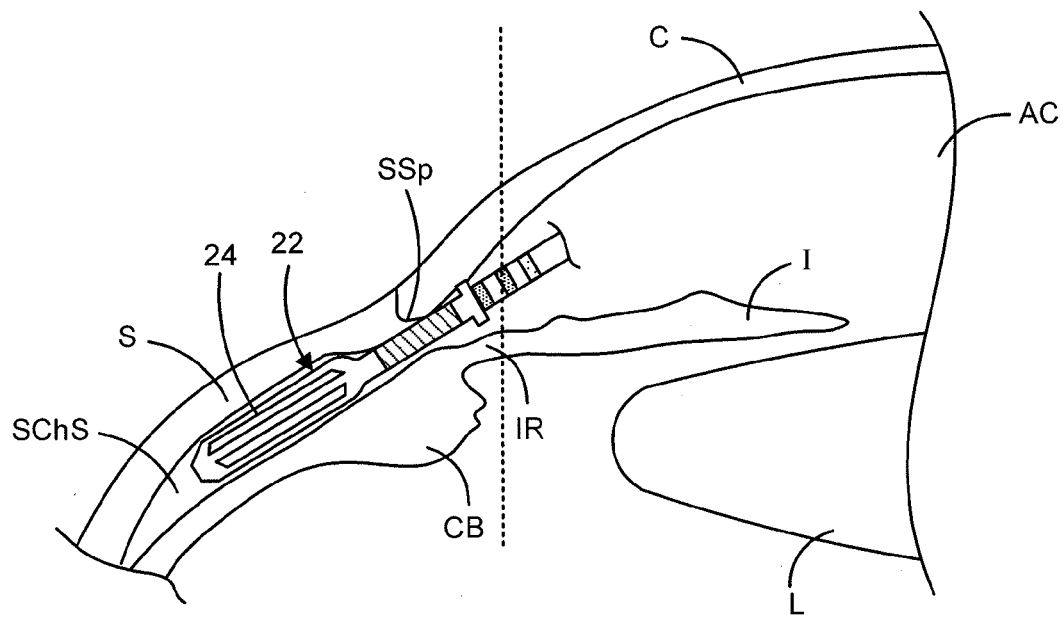
FIG. 20 shows an example of at least a part of the expandable features of the expandable implant positioned in the suprachoroidal space with the expandable features in an expanded configuration.

Once at least a part of one or more expandable features of the expandable implant 22 are positioned in the suprachoroidal space, the one or more restraints may be released in order to allow the expandable implant 22 to enter into an expanded configuration, as shown in FIG. 20. In an expanded configuration, the expandable features 24 of the expandable implant 22 can assist in increasing the separation between the sclera and choroid than what was achieved prior to expansion of the expandable implant 22. As described above, the increase in separation between the sclera and choroid can assist in reducing IOP in an eye, such as an eye suffering from glaucoma.

Once properly positioned in an expanded configuration, the expandable implant 22 can then be released from the guidewire 58. The expandable implant 22 can be released, for example, by withdrawing the guidewire 58 such that the expandable implant 22 is effectively disengaged in a controlled manner from the tip of the guidewire 58 with the sheath 60.

The expandable implant 22 can include one or more structural features near its proximal region that aid to anchor or retain the implant 105 in the target region in the eye. The structural features can include flanges, protrusions, wings, tines, or prongs, and the like that can lodge into the surrounding eye anatomy to retain the expandable implant 22 in place and prevent the expandable implant 22 from moving further into the suprachoroidal space SchS.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination.

Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

What is claimed is:

1. A device for implanting in an eye, comprising:
an expandable sheath formed of an elongate, tubular body having at least one expandable feature configured to form an expanded and a compact configuration, the at least one expandable feature including at least two longitudinal, non-intersecting struts each extending from a proximal collar to a distal collar, and wherein the at least one of the proximal collar and distal collar is adaptable to an ocular implant, wherein the implant includes a second elongate tubular body configured to be implanted in an eye and wherein at least one of the proximal collar and the distal collar is fixedly attached to the second tubular body of the device and the other of the proximal collar and the distal collar is movably attached to the second tubular body of the device such that the distal collar slides co-axially along a longitudinal axis of the second tubular body.

2. The device of claim 1, wherein at least the expandable features are made out of a medical grade shape memory material, such as nitinol or a shape memory polymer.

3. The device of claim 1, wherein the expandable sheath is formed out of a laser cut nitinol material.

4. The device of claim 1, wherein at least a part of a surface of the expandable sheath is treated with a plasma cleaning process.

5. The device of claim 1, wherein at least a part of a surface of the expandable sheath is treated with a laser ablation process.

6. The device of claim 5, wherein the surface treated with the laser ablation process includes at least one ribbed feature.

7. The device of claim 1, wherein the compact configuration has an outside diameter dimension in the range of 0.4 millimeter to 0.6 millimeter.

8. The device of claim 1, wherein the expanded configuration has an outside diameter dimension in the range of 2.0 millimeters to 3.0 millimeters.

9. The device of claim 1, wherein the expandable sheath includes at least one drug.

10. The device of claim 9, wherein the expandable sheath is adapted to an implant that does not include a drug.

11. A method, comprising:
providing an expandable sheath, wherein the expandable sheath includes at least one expandable feature configured to form an expanded and a compact configuration, the at least one expandable feature including at least two longitudinal, non-intersecting struts each extending from at least one of a proximal collar and a distal collar, and wherein the at least one of the proximal collar and distal collar is configured to attach to an ocular implant;
attaching the expandable sheath to the implant;
implanting the implant and the expandable sheath into an eye
sliding at least one of the proximal collar and distal collar co-axially along a longitudinal axis of the expandable sheath to expand the struts.

12. The method of claim 11, wherein the at least one expandable feature is in a compact configuration during implantation of the expandable sheath and forms an expanded configuration after implantation into the eye.

13. The method of claim 11, wherein the implant includes an elongate tubular body configured to be implanted in an eye.

14. The method of claim 11, wherein at least the expandable features are made out of a medical grade shape memory material, such as nitinol or a shape memory polymer.

15. The method of claim 11, wherein the expandable sheath is formed out of a laser cut nitinol material.

16. The method of claim 11, wherein at least a part of a surface of the expandable sheath is treated with a plasma cleaning process.

17. The method of claim 11, wherein at least a part of a surface of the expandable sheath is treated with a laser ablation process.

18. The method of claim 17, wherein the surface treated with the laser ablation process includes at least one ribbed feature.

19. The device of claim 11, wherein the expandable sheath includes at least one drug.

20. The device of claim 19, wherein the expandable sheath is adapted to an implant that does not include a drug.

* * * * *